US007972336B2

(12) United States Patent
James et al.

(10) Patent No.: US 7,972,336 B2
(45) Date of Patent: Jul. 5, 2011

(54) METHODS FOR TREATING FRACTURES OF THE FEMUR AND FEMORAL FRACTURE DEVICES

(75) Inventors: Anthony H. James, Bartlett, TN (US); R. Keith McReynolds, Olive Branch, MS (US); Joseph M. Ferrante, Bartlett, TN (US); Kohsuke Watanabe, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 821 days.

(21) Appl. No.: 11/894,234

(22) Filed: Sep. 18, 2007

(65) Prior Publication Data
US 2008/0077142 A1  Mar. 27, 2008

Related U.S. Application Data

(62) Division of application No. 11/090,102, filed on Mar. 28, 2005, now abandoned.

(60) Provisional application No. 60/557,027, filed on Mar. 26, 2004.

(51) Int. Cl.
*A61B 17/72* (2006.01)
(52) U.S. Cl. ............... 606/62; 606/64; 606/65
(58) Field of Classification Search ............ 606/62–68; 403/122, 127, 131
See application file for complete search history.

(56) References Cited

U.S. PATENT DOCUMENTS

| | | | |
|---|---|---|---|
| 2,439,995 A | 4/1948 | Thraikill |
| 2,441,765 A | 5/1948 | Hopkins |
| 2,496,126 A | 1/1950 | Haboush |
| 2,526,959 A | 10/1950 | Lorenzo |
| 2,702,543 A | 2/1955 | Pugh et al. |
| 2,834,342 A | 5/1958 | Yost |
| 3,094,120 A | 6/1963 | Blosser |
| 3,308,812 A | 3/1967 | Gidlund |
| 3,374,786 A | 3/1968 | Callender, Jr. |
| 3,554,193 A | 1/1971 | Konstantinou |
| 3,842,825 A | 10/1974 | Wagner |
| 4,011,603 A | 3/1977 | Steffee |
| 4,095,591 A | 6/1978 | Graham, Jr. et al. |
| 4,432,358 A | 2/1984 | Fixel |
| 4,530,355 A | 7/1985 | Griggs |
| 4,612,920 A | 9/1986 | Lower |

(Continued)

FOREIGN PATENT DOCUMENTS

DE   1 265 339   4/1968

(Continued)

OTHER PUBLICATIONS

Michael R. Baumgaertner, M.D., Compression Hip Screw Plates and Nails, Surgical Technique, Aug. 1998, Smith & Nephew, Inc., pp. 1-80 (Mar. 1998).

(Continued)

*Primary Examiner* — Thomas C Barrett
*Assistant Examiner* — Nicholas Woodall
(74) *Attorney, Agent, or Firm* — David A. Warmbold; David A. Chambers

(57) ABSTRACT

The present invention relates to methods and devices for treating femoral fractures, wherein a polyaxial cross member is employed to accommodate a wide range of angles and anteversions/retroversions in the femur, and different securing mechanisms can also be employed to hold and retain such polyaxial cross member in place at the desired orientation.

13 Claims, 23 Drawing Sheets

U.S. PATENT DOCUMENTS

| | | |
|---|---|---|
| 4,827,917 A | 5/1989 | Brumfield |
| 4,988,350 A | 1/1991 | Herzberg |
| 5,032,125 A | 7/1991 | Durham et al. |
| 5,127,914 A | 7/1992 | Calderale et al. |
| 5,429,640 A | 7/1995 | Shuler et al. |
| 5,462,547 A | 10/1995 | Weigum |
| 5,484,439 A | 1/1996 | Olson et al. |
| 5,549,608 A | 8/1996 | Errico et al. |
| 5,607,426 A | 3/1997 | Ralph et al. |
| 5,653,709 A | 8/1997 | Frigg et al. |
| 5,662,667 A | 9/1997 | Knodel |
| 5,871,485 A | 2/1999 | Rao et al. |
| 5,876,402 A | 3/1999 | Errico et al. |
| 5,888,204 A | 3/1999 | Ralph et al. |
| 5,954,722 A | 9/1999 | Bono |
| 6,007,536 A | 12/1999 | Yue |
| 6,123,708 A * | 9/2000 | Kilpela et al. ............ 606/62 |
| 6,139,552 A | 10/2000 | Horiuchi et al. |
| 6,221,074 B1 | 4/2001 | Cole et al. |
| 6,235,034 B1 | 5/2001 | Bray |
| 6,238,126 B1 | 5/2001 | Dall |
| 6,413,259 B1 | 7/2002 | Lyons et al. |
| 6,468,278 B1 | 10/2002 | Muckter |
| 6,669,697 B1 | 12/2003 | Pisharodi |
| 6,893,444 B2 | 5/2005 | Orbay |
| 6,902,567 B2 | 6/2005 | Del Medico |
| 6,945,975 B2 | 9/2005 | Dalton |
| 6,979,334 B2 | 12/2005 | Dalton |
| 7,135,023 B2 | 11/2006 | Watkins et al. |
| 2002/0143338 A1 | 10/2002 | Orbay et al. |
| 2002/0151898 A1 | 10/2002 | Sohngen et al. |
| 2002/0161370 A1 | 10/2002 | Frigg et al. |
| 2004/0186474 A1 | 9/2004 | Matthis et al. |
| 2004/0220566 A1 | 11/2004 | Bray |
| 2004/0220570 A1 | 11/2004 | Frigg |
| 2005/0010224 A1 | 1/2005 | Watkins et al. |
| 2005/0192580 A1 | 9/2005 | Dalton |
| 2005/0234457 A1 | 10/2005 | James |
| 2005/0283154 A1 | 12/2005 | Orbay et al. |
| 2006/0122605 A1 | 6/2006 | Suh et al. |
| 2006/0149253 A1 | 7/2006 | Doubler et al. |
| 2006/0293668 A1 | 12/2006 | May et al. |
| 2007/0010817 A1 | 1/2007 | De Coninck |
| 2007/0233100 A1 | 10/2007 | Metzinger |
| 2007/0233103 A1 | 10/2007 | Metzinger |
| 2007/0233104 A1 | 10/2007 | Metzinger |
| 2007/0233116 A1 | 10/2007 | Olerud |
| 2008/0108992 A1 | 5/2008 | Barry et al. |
| 2009/0149888 A1 | 6/2009 | Abdelgany |
| 2009/0192549 A1 | 7/2009 | Sanders et al. |

FOREIGN PATENT DOCUMENTS

| | | |
|---|---|---|
| DE | 19610741 C1 | 11/1997 |
| EP | 0 382 256 A1 | 8/1990 |
| EP | 0828459 A1 | 3/1998 |
| EP | 1364623 A1 | 11/2006 |
| FR | 2860420 A1 | 4/2005 |
| GB | 1 231 918 A | 5/1971 |
| GB | 2 090 745 A | 7/1982 |
| JP | 09 220235 A | 8/1997 |
| JP | 2001-149379 | 6/2001 |
| WO | WO9632071 | 10/1996 |
| WO | WO 01/91660 | 12/2001 |
| WO | WO2005018471 A1 | 3/2005 |
| WO | WO2008141805 A2 | 11/2008 |

OTHER PUBLICATIONS

VHS® Vari-Angle Hip Screw System, pp. 2 and 3 (undated).

* cited by examiner

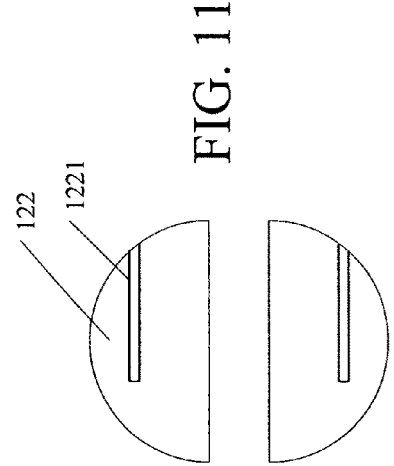
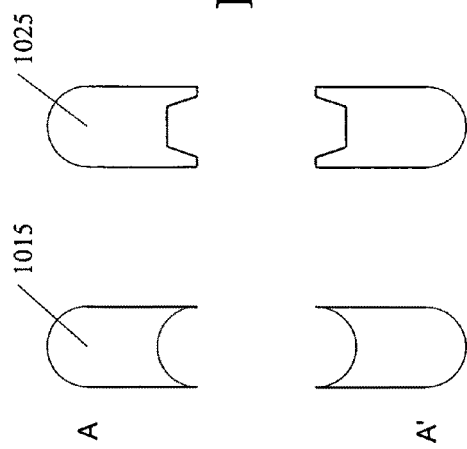
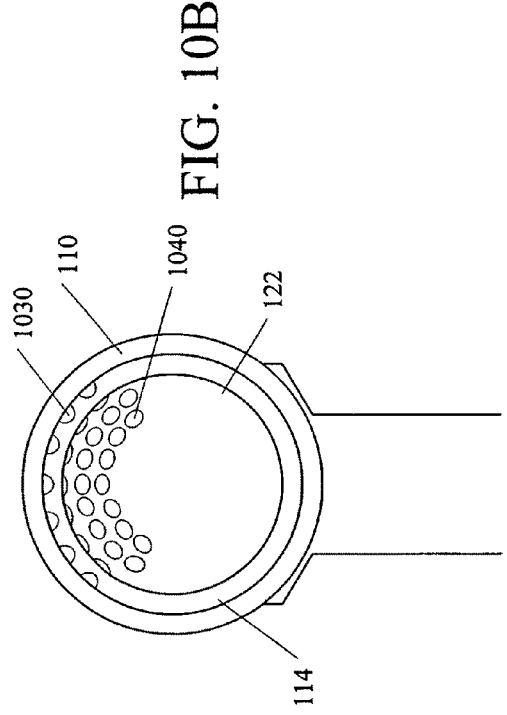

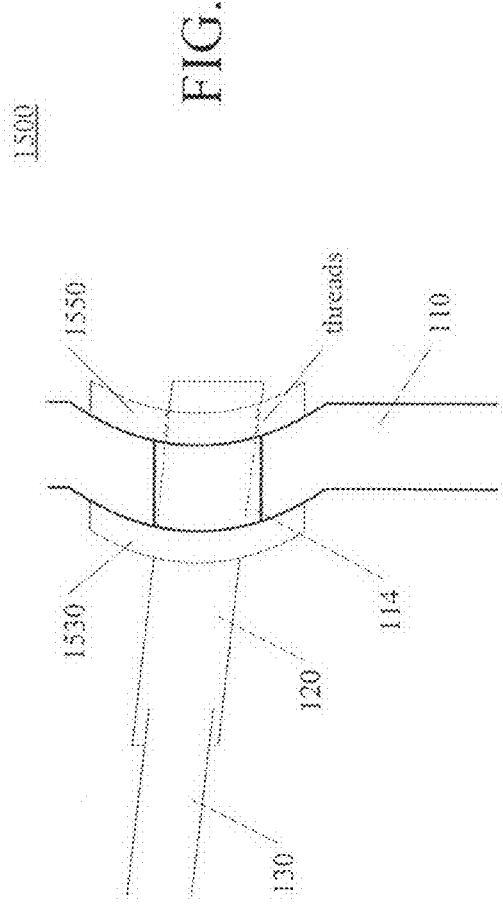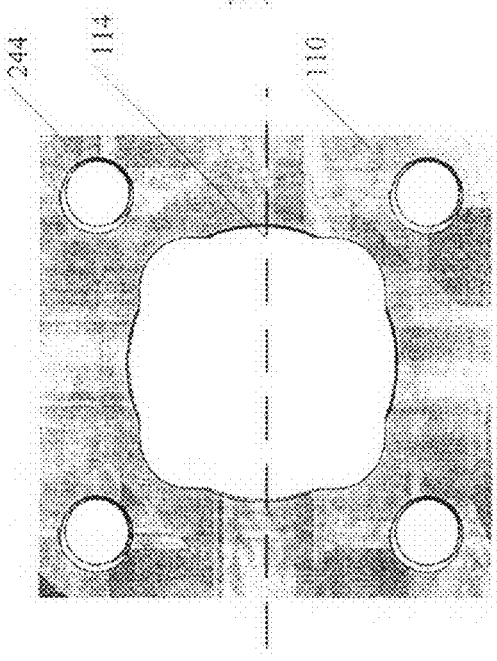

METHODS FOR TREATING FRACTURES OF THE FEMUR AND FEMORAL FRACTURE DEVICES

PRIORITY INFORMATION

This application is a divisional application of U.S. patent application Ser. No. 11/090,102 filed Mar. 28, 2005 now abandoned entitled "Methods for Treating Fractures of the Femur and Femoral Fracture Devices," which claims priority to U.S. Provisional Patent Application No. 60/557,027, filed Mar. 26, 2004, entitled, "Compression Hip Screw and Intramedullary Nail with Polyaxial Adjustable Neck Screw," both of which are incorporated by reference in their entirety.

BACKGROUND OF THE INVENTION

1. Field of the Invention

The present invention relates generally to methods and devices for treating femoral fractures. More specifically, the present invention relates to the use of novel compression hip screw and intramedullary nail assemblies with a polyaxial cross member for treating fractures to the femur.

2. Background of the Invention

There are a variety of devices used to treat femoral fractures. Fractures of the neck, head or intertrochanter of the femur have been successfully treated with a variety of compression hip screw and intramedullary nail assemblies. A common compression hip screw (CHS) assembly generally includes a side plate having a barrel member, a lag screw, and a compression screw. The side plate is secured to the exterior of the femur, and the barrel member is inserted into a pre-drilled hole at a proper angle in the direction of the femoral head. The lag screw, which has a threaded end and a smooth portion, is inserted through the barrel member so that it extends across the break or fracture line and into the femoral head. The threaded portion engages the femoral head. The compression screw connects the lag screw to the plate. By adjusting the tension of the compression screw, the active compression or reduction of the fracture can be adjusted. The smooth portion of the lag screw is free to slide through the barrel member to permit the adjustment of the compression screw for active compression. Furthermore, under load of a patient's body weight, while proper angulation of the femoral head is maintained, the lag screw can slide inside the barrel member to allow the fractured sides of the break to bear on each other for passive compression and optimal healing of the fracture. Some examples of CHS assemblies are the Ambi Classic compression hip screw assembly manufactured by Smith & Nephew Inc. of Memphis, Tenn., and those shown in Fixel, U.S. Pat. No. 4,432,358; Callender, Jr., U.S. Pat. No. 3,374,786; Pugh et al., U.S. Pat. No. 2,702,543; Griggs, U.S. Pat. No. 4,530,355; Blosser, U.S. Pat. No. 3,094,120; and Wagner, U.S. Pat. No. 3,842,825.

A typical intramedullary nail assembly generally includes an intramedullary rod and a cross member directed toward the femoral head. The intramedullary rod is inserted into the marrow canal of the femur. The angled cross-member is inserted through the femur and a proximal end of the intramedullary rod. Some examples of the intramedullary nail assemblies are the Russell-Taylor (RT) reconstruction nail assembly and IMHS (intramedullary hip screw) assembly manufactured by Smith & Nephew Inc. of Memphis, Tenn. A description of the IMHS assembly is in U.S. Pat. No. 5,032,125, issued on Jul. 16, 1991 to Durham et al., which is herein incorporated by reference in its entirety. As with the common CHS assembly mentioned earlier, both the RT reconstruction nail and the IMHS assemblies allow: a) active sliding compression that surgeons can apply during surgery to reduce the fracture; and b) passive sliding compression under load of a patient's body weight. While the IMHS assembly employs a barrel member similar in some ways to the barrel member in the common CHS assembly, the RT reconstruction nail relies on its own structure without any barrel to provide the active/passive sliding compression.

SUMMARY OF THE INVENTION

Summary of the Problems

The aforementioned conventional devices have a fixed-angle opening oriented toward the femoral head, through which the sliding lag screw or cross-member is inserted. As a result, the lag screw or cross member can only be oriented at a single fixed angle relative to the side plate or intramedullary rod. Thus, when treating proximal femur fractures with such devices, surgeons are limited to using implants with a fixed anteversion/retroversion, regardless of the patient anatomy, which can vary significantly from one patient to the next. Such a limitation frequently leads to suboptimal cross member placement, which can lead to screw cut-out through the femoral head and further damage the proximal femur. Constrained by the fixed anteversion/retroversion in conventional femur fracture devices, surgeons could resort to making adjustments to accommodate a patient's anatomy by contouring the side plate, if a compression hip screw assembly is used; or aligning the intramedullary rod, if an intramedullary nail assembly is used, to properly situate the fixed-angle lag screw across the fracture in the femur. However, such adjustments often require additional surgical operations to the muscles and tissues surrounding the proximal femur that would pose further health risks to the patient. There exists a compression hip screw assembly with a variable neck angle named VHS™ (variable hip screw) from Biomet of Warsaw, Ind. However, such device uses a high-profile worm gear mechanism for angle adjustment and does not allow for continuously variable retroversion/anteversion.

Summary of the Solutions

The present invention advantageously addresses at least the above needs and other needs by providing methods for treating fractures of the femur and femoral fracture devices that can accommodate variances in a patient's anatomy through the use of a polyaxial adjustable cross member.

Accordingly, in one embodiment of the present invention, there is provided an apparatus for treating fractures of the femur comprising: a first plate configured to secure to an exterior of a femur, the first plate providing a first opening; an extended portion having a polyaxial joint affixed at one end, the extended portion configured to extend through the first opening; a cross member configured for insertion into the extended portion to permit sliding compression of a fracture of the femur and rotation about a plurality of axes as provided by the polyaxial joint; and a securing mechanism configured to lock the polyaxial joint at a predetermined orientation in the first opening.

In another embodiment of the present invention, there is provided an apparatus for treating fractures of the femur comprising: an intramedullary rod having a proximal end and a distal end and configured for insertion into the marrow canal of the femur, the intramedullary rod including a proximal pair of openings closer to the proximal end than to the distal end; a spherical joint inserted internal to the intramedullary rod near the proximal pair of openings in the intramedullary rod; a cross member configured for insertion through the proximal pair of openings and the spherical joint to permit sliding compression of a fracture of the femur and rotation about a plurality of axes as provided by the spherical joint; and a securing mechanism internal to the intramedullary rod and configured to lock the polyaxial joint at a predetermined orientation in the first opening.

Alternative embodiments include the use of different securing mechanisms to lock the polyaxial joint in place and methods for using the same.

BRIEF DESCRIPTION OF THE DRAWINGS

The preferred embodiments are illustrated by way of example and not limited in the following figure(s), in which:

FIGS. 10A-B depict various configurations for the side wall or inner surface of an opening in the side plate of a polyaxial CHS assembly, in accordance with one embodiment of the present invention;

FIG. 11 depicts an embodiment of a polyaxial joint for use in a compression hip screw (CHS) assembly, in accordance with another embodiment of the present invention;

FIG. 15 depicts aspects of a polyaxial CHS assembly, in accordance with another embodiments of the present invention;

FIG. 23 depicts an exemplary shape for an opening in the side plate of a compression hip screw assembly, in accordance with an embodiment of the present invention.

DETAILED DESCRIPTION OF THE INVENTION

Reference is now made in detail to embodiments of the present invention, aspects of certain illustrative embodiments of which are illustrated in the accompanying drawings, in which like numerals indicate like elements, showing femoral fracture devices with a polyaxial adjustable cross member that can: a) rotate about a wide range of angles and anteversion/retroversions during treatments for optimal angular placement of such cross member across the fracture site; and b) withstand high weight-bearing loads once its optimal angular placement is set to prevent undesirable axial and bending moments. Among other advantages in certain cases, but not necessary to the operation or structure of any particular embodiments or devices according to the invention, cut-out of such cross member through the femoral head can be reduced. In other cases, although once again this aspect is not necessary to operation or structure of any particular embodiments or devices according to the invention, inventory of parts for femoral fracture devices of the present invention can also be substantially reduced because a one-size device can be used for different angles and anteversions/retroversions.

Figure 1:
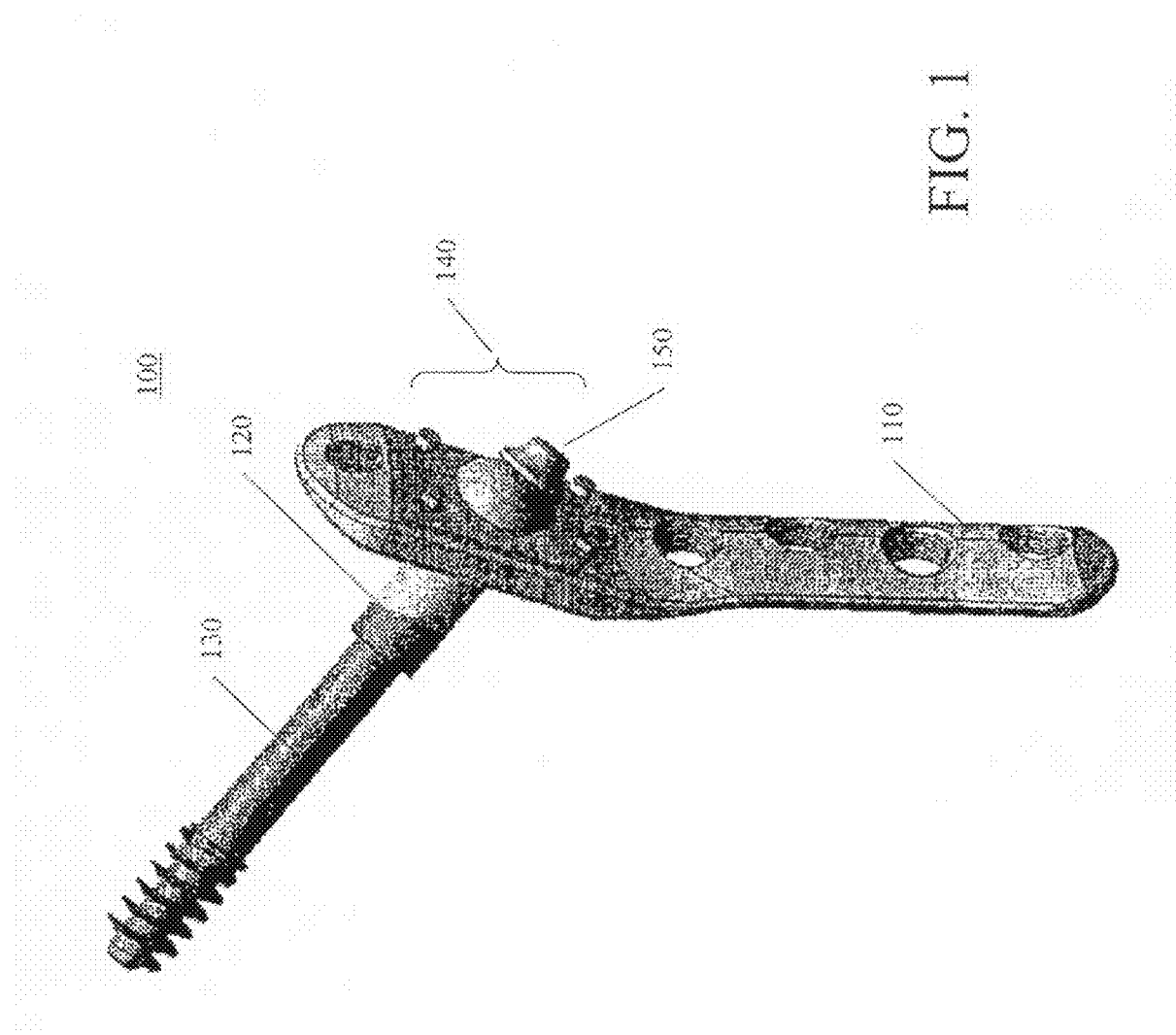
FIG. 1 depicts aspects of a polyaxial compression hip screw (CHS) assembly, in accordance with one embodiment of the present invention.
Figure 2:
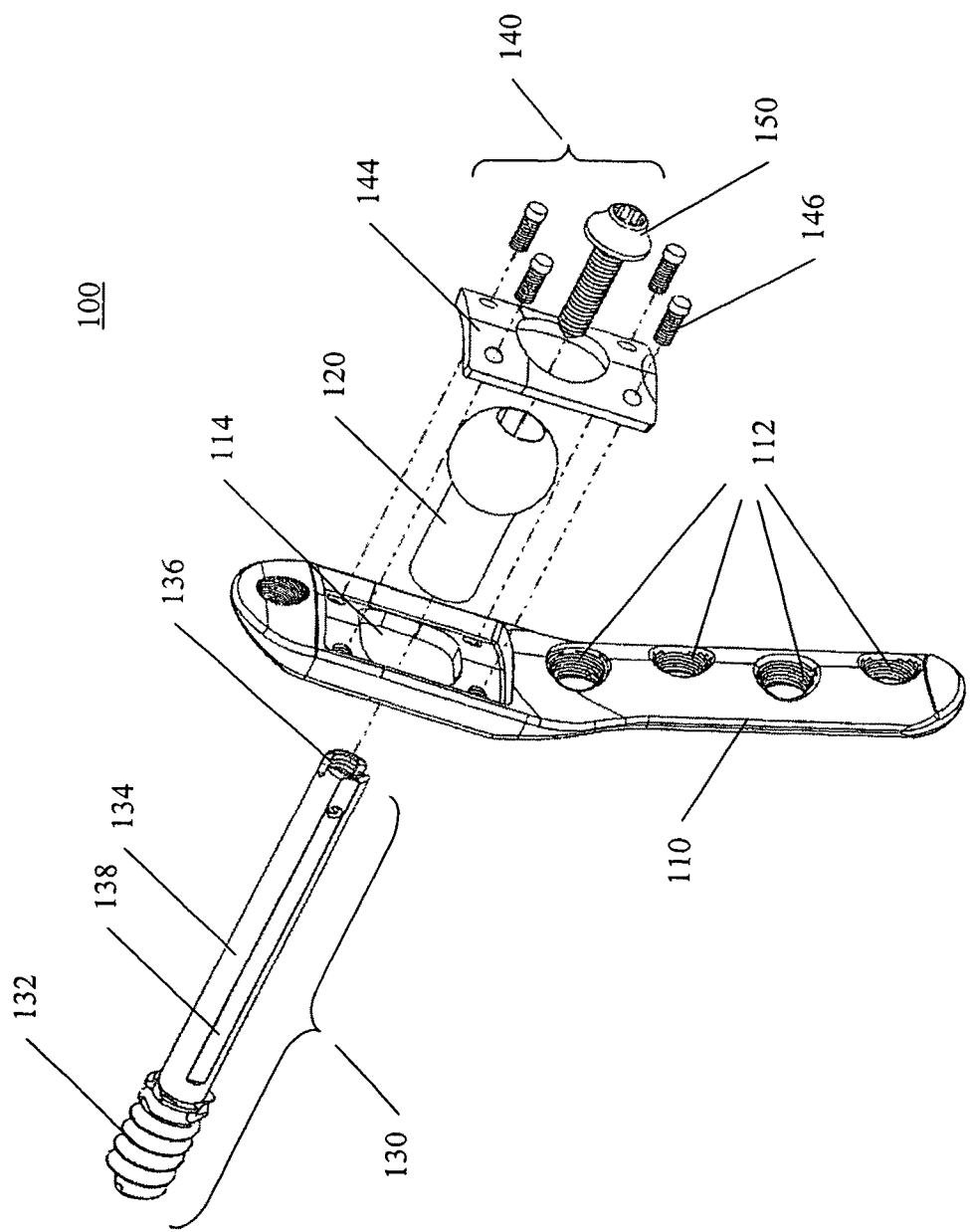
FIG. 2 depicts the polyaxial CHS assembly shown in FIG. 1, broken down into its various components, in accordance with an embodiment of the present invention.

FIG. 1 depicts aspects of a polyaxial compression hip screw (CHS) assembly 100 having a polyaxial cross member in accordance with one embodiment of the present invention. This particular polyaxial CHS assembly 100 includes a side plate 110, a barrel member 120, a cross member 130, a compression screw 150, and a securing mechanism 140. FIG. 2 depicts the compression hip screw assembly 100 of FIG. 1, broken down into its various components. The side plate 110 is a support plate and, preferably, it can be contoured for contacting and securing to the exterior of the fractured proximal femur of a patient via, e.g., screws into the holes 112. In one embodiment, the side plate 110 can also be a compression plate. Holes 112 can be threaded, or unthreaded, or a combination of both, to allow screws to operate as fixation screws or compression screws. As one example, some holes can be threaded for fixation screws, to form a rigid screw/plate construct, and some holes can be unthreaded to receive compression screws, for active compression during surgery. As another example, some or all holes can include a threaded portion and a non-threaded portion to receive either compression or fixation screws.

The barrel member 120 is an extended portion that incorporates a spherical or ball joint 122 on one end and extends through an opening 114 in the side plate 110. The ball joint 122 is allowed to pivot, preferably but not necessarily continuously, in a polyaxial manner in the opening 114 through a predetermined range of motion in preferably multiple degrees of rotational freedom. Accordingly, the ball joint 122 can have a potentially infinite number of positions across its range of motion relative to the opening 114; alternatively, structure such as detents or other desired features can be included to cause the ball joint 122 to cooperate with the opening 114 in a manner that only allows certain settings, such as certain degrees of angulation relative to the side plate 110. The cross member 130 is a component that is able to engage the proximal portion of the femur, such as the femoral head. In one embodiment, the cross member 130 can be a lag screw and is described and illustrated as such throughout the present disclosure for simplicity. However, alternative embodiments are contemplated wherein the cross member 130 can be any fastening element, with or without threads, that can engage and anchor to the proximal portion of the femur, such as the femoral head. The lag screw 130 includes a threaded end 132 and a smooth portion 134. It is inserted through the barrel member 120 and extends across the fracture line and into the femoral head. In the particular embodiment shown, the compression screw 150 secures the lag screw 130, via the threaded bore 136, within the barrel member 120 and/or ball joint 122. By adjusting the tension of the compression screw 150, the compression (reduction) of the fracture can be adjusted. The smooth portion 134 of the lag screw 130 is free to slide through the barrel member 120 to permit the adjustment of the compression screw 150 during active compression. The smooth portion 134 also provides for sliding compression of the fracture site due to the patient's weight-bearing and muscle forces.

The securing mechanism 140 includes a securing element 144, such as a top plate, and one or more fastening elements 146, such as screws, that secure the barrel member 120 to an end of the side plate 110, which can have a depression around the opening 114 to accommodate and if desired, help urge the top plate 144 toward the outer surface of the side plate 110. In operation, the lag screw 130 is inserted at a proper angle relative to the femur to engage, for example, the femoral head. Once the proper angle is achieved, the barrel member 120 with its ball joint 122 is inserted through the opening 114 in the side plate 110 and over the lag screw 130 until the side plate 110 is in contact with the lateral side of the femur. At this juncture, the side plate 110 can be adjusted in multiple planes until it fits, preferably flush, to the side of the femur. The securing mechanism 140 is then engaged; in this case, the screws 146 are tightened to press the top plate 144 against the side plate 110 and bias the ball joint 122 against the side wall of the four-sided opening 114 so that the ball joint 122 make contact with such side wall at one or more areas to hold or retain the ball joint 122 in place at the desired orientation. The surgery is continued and completed in a standard manner.

As a body implant, the polyaxial CHS assembly 100 can be subje'cted to high weight-bearing loads with combined axial (rotational) and bending (downward and off-axis) components. For example, according to some accounts, the lag screw 130 can be subjected to three times the patient's body weight every time the patient takes a step, with a typical cyclical loading of approximately one million times (i.e., steps) a year over the life cycle of the implant (some are never removed); and to even higher loads for more strenuous activities such as stair climbing and running. Such high weight-bearing loads can cause undesirable rotation of the lag screw 130 about its long axis, overwhelm the securing mechanism 140, and shift the ball joint 122 away from the desired orientation. Hence, an anti-rotation aspect can be incorporated into the polyaxial CHS assembly to prevent the rotation of its cross member. In the particular polyaxial CHS assembly 100, the lag screw 130 is keyed with a depression 138, that is preferably flat with two side walls, along its long axis, as shown in FIG. 2. Correspondingly, internal to barrel member 120 is a protrusion (not shown) that extends out from the inner wall of the barrel member 120 and into the depression 138 when the lag screw 130 is inserted through the barrel member 120. Thus, such protrusion is bounded by the side walls of the depression 138, and the lag screw 130 is prevented from rotating once its threaded end 132 is engaged in the femoral head to keep the femoral head from rotating and/or the threads end 132 from rotating out of the bone. However, the rotational stress that urges a rotation of the lag screw 130 is now further imparted on the ball joint 122.

To withstand the expected high weight-bearing loads and the resulting rotational stress to the lag screw 130 as discussed above, the polyaxial CHS assembly 100 can be designed with proper geometric configurations as already described above and further described later. Additionally, suitable types of material having proper tensile strength and kinds of surface texture for the various components of such a polyaxial CHS assembly can be chosen in light of the expected loads. Additional embodiments of a polyaxial CHS assembly are further described below.

Figure 3:
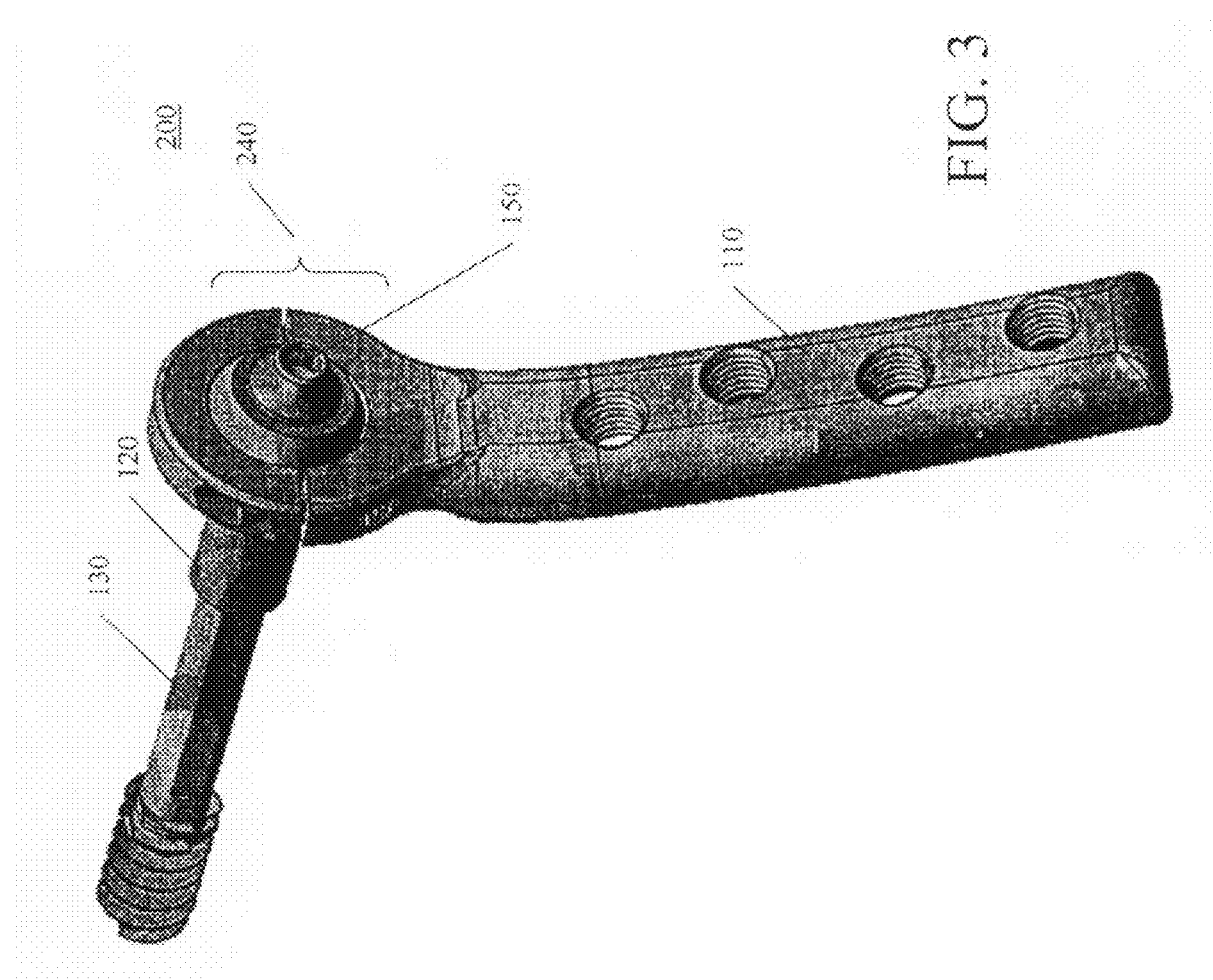
FIG. 3 depicts aspects of a polyaxial CHS assembly, in accordance with another embodiment of the present invention.
Figure 4:
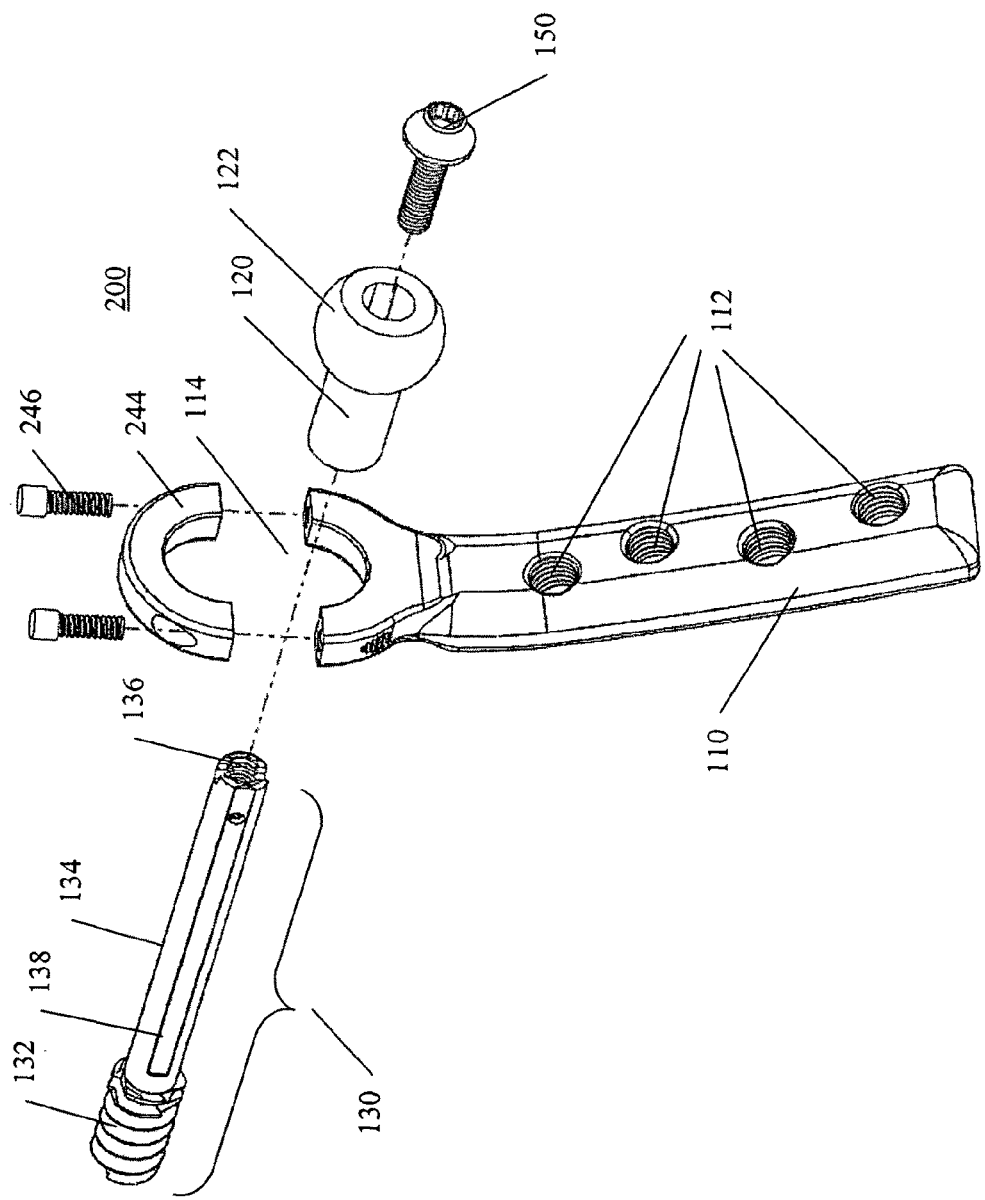
FIG. 4 depicts the polyaxial CHS assembly shown in FIG. 2, broken down into its various components, in accordance with an embodiment of the present invention.

FIG. 3 depicts aspects of a polyaxial CHS assembly 200 with a polyaxial cross member in accordance with another embodiment of the present invention. The polyaxial CHS assembly 200 functions similarly to the assembly 100 depicted in FIG. 1, with like numerals indicating like elements, except for the securing mechanism 240. FIG. 4 depicts the polyaxial CHS assembly 200, broken down into its various components to further illustrate the securing mechanism 240. In this particular polyaxial CHS assembly 200, the securing mechanism 240 includes a securing element 244, such as a generally concave-shaped clamp, and one or more fastening elements 246, such as screws, that clamp down to the side plate 110 and secure the ball joint 122 to the side plate 110. The clamp 244 cooperates with one end of the side plate 110 to form an opening 114, for example a circular opening, in which the ball joint 122 can pivot in a polyaxial manner. Once the lag screw 130 is situated at a proper angle relative to the femur, and the side plate 110 is adjusted as described earlier, the one or more screws 246 are tightened in the opposing screw slots in the clamp 244 and side plate 110 to bias the ball joint 122 against the side wall of the opening 114 so that the ball joint 122 can make contact with such side wall at one or more areas to hold and retain the ball joint 122 in place at the desired orientation.

Although FIGS. 3 and 4 depict a clamp 244 that cooperates with the side plate 110 to form the circular opening 114, alternative embodiments are contemplated wherein the opening 114 can have different shapes, with clamp 244 and one end of the side plate having different shapes to form the shape of the opening 114. The different shapes for the opening 114 can be devised as desired such that the opening 114 can provide a proper seat for the ball joint 122 and contact the ball joint 122 at one or more areas to assist in maintaining the ball joint 122 at the desired orientation under high-weight bearing loads as discussed earlier. For example, the clamp 244 and one end of the side plate 110 can both have half-rectangular shapes that cooperate with each other to form a rectangular-shaped opening 114 similar to the same one shown in FIG. 2. In another example, the clamp 244 and the end of the side plate 110 can have shapes that cooperate with each other to form an opening 114 in the shape shown in FIG. 23. Additionally, the clamp 244 and the end of the side plate 110 can have shapes different from each other.

Figure 5:
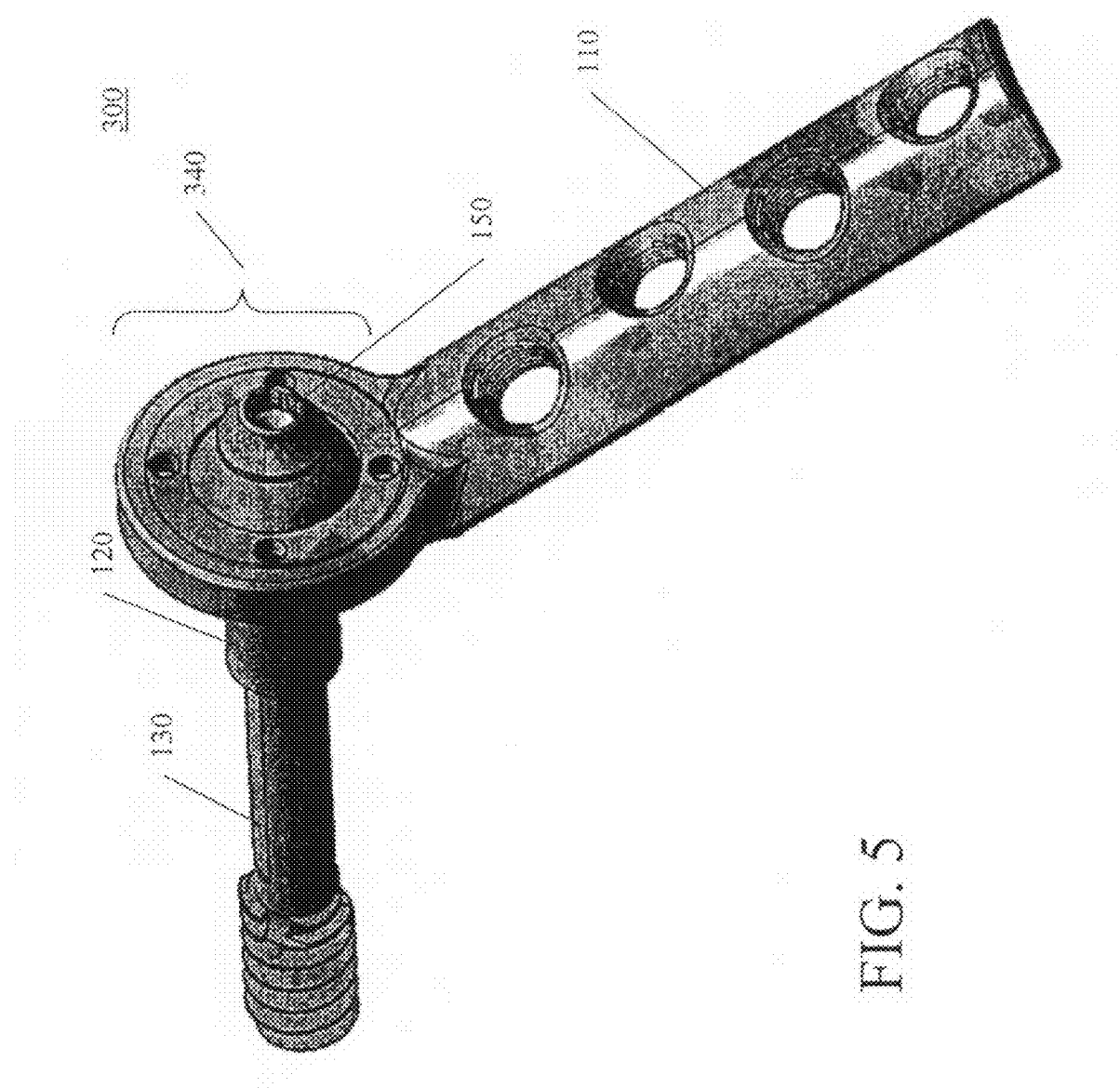
FIG. 5 depicts aspects of a polyaxial CHS assembly, in accordance with another embodiment of the present invention.
Figure 6:
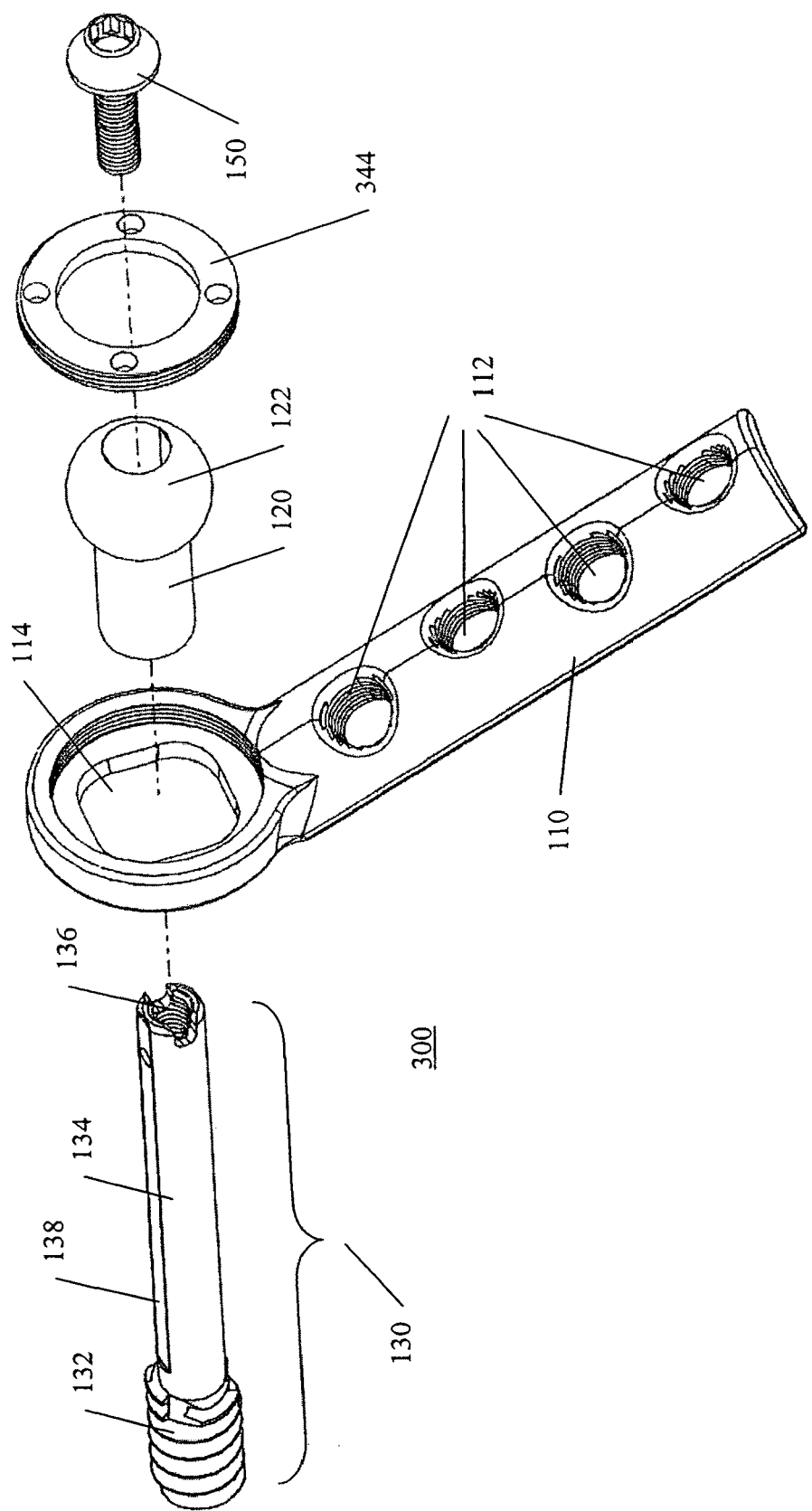
FIG. 6 depicts the polyaxial CHS assembly shown in FIG. 5, broken down into its various components, in accordance with an embodiment of the present invention.

FIG. 5 depicts aspects of a CHS assembly 300 with a polyaxial cross member in accordance with still another embodiment of the present invention. The polyaxial CHS assembly 300 functions similarly to the assemblies 100 and 200 shown in FIGS. 1 and 3, with like numerals indicating like elements, except for the securing mechanism 340. FIG. 6 depicts the polyaxial CHS assembly 300, broken down into its various components to further illustrate the securing mechanism 340. As shown, the securing mechanism 340 includes a securing element 344, such as a top plate, that can be threaded to one end of the side plate 110 to secure the ball joint 122 to the side plate 110. Also as shown, the top plate 344 includes holes on its surface to which a tool can be applied to turn the top plate 344. However, alternative embodiments are contemplated in which the top plate 344 can be adapted for any tool to be used to turn the top plate 344. Once the lag screw 130 is inserted at the proper angle as mentioned earlier, the top plate 344 is threaded tightly to the one end of the side plate 110 to bias the ball joint 122 against the side wall of the opening 114 so that the ball joint 122 can make contact with such side wall at one or more areas to hold and retain the ball joint 122 in place at the desired orientation.

Figure 16:
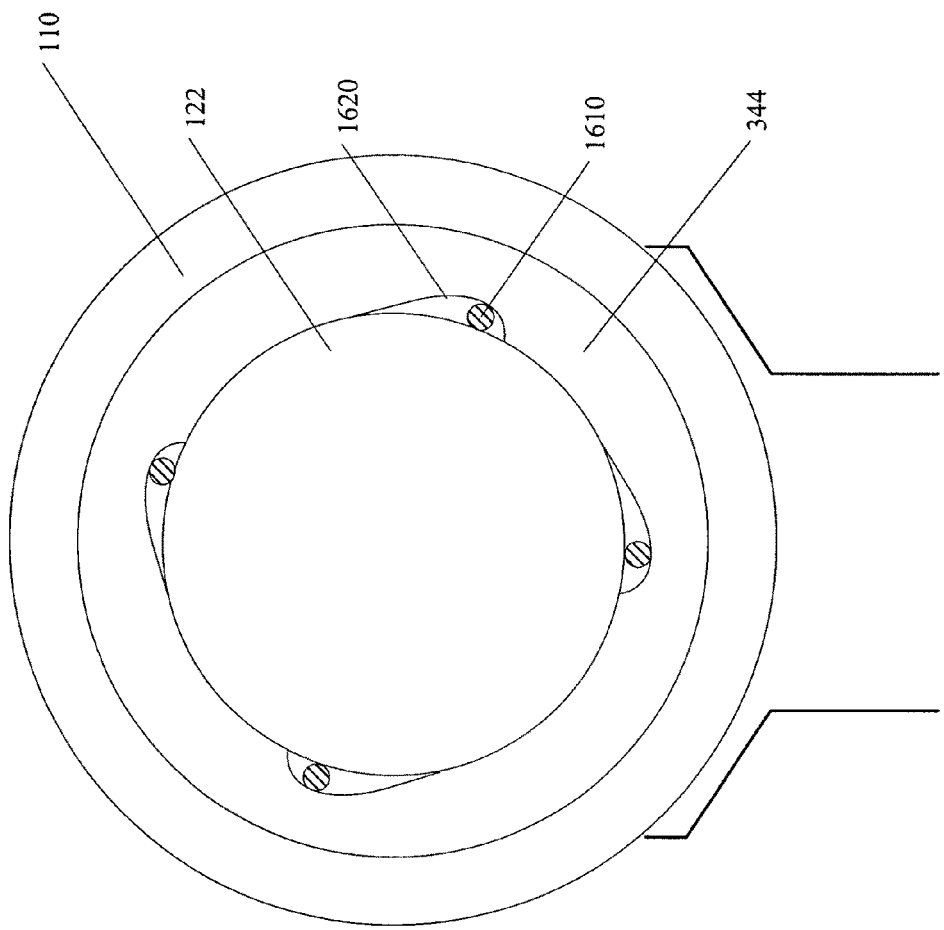
FIG. 16 depicts aspects of a polyaxial CHS assembly, in accordance with another embodiment of the present invention.

In addition to the top plate 344 being threaded, it can have an internal design that includes one or more ball bearings 1610 placed in one or more angled slots 1620 as shown in FIG. 16. In this embodiment, as the top plate 344 is turned in one direction, e.g., clockwise, to engage the side plate 110 and the ball joint 122, each bearing 1610 rolls along its respective angled slot 1620 in the other direction, e.g., counterclockwise, until it reaches a stopping position, whereby it is compressed between the ball joint 122 and the wall of its respective angled slot 1620. Thus, such compression further holds or maintains the ball joint 122 in place at the desired orientation.

Figure 7:
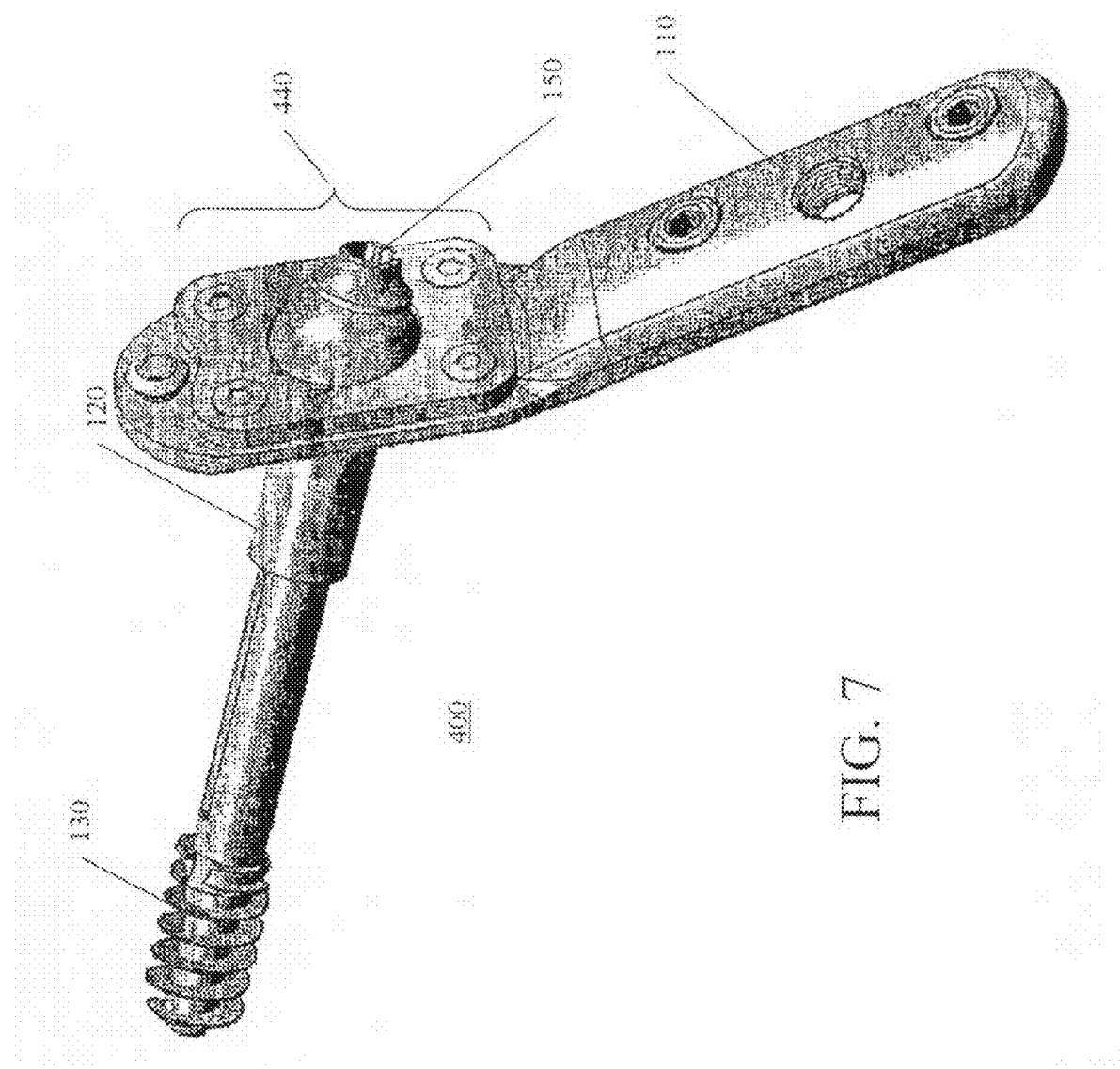
FIG. 7 depicts aspects of a polyaxial CHS assembly, in accordance with another embodiment of the present invention.
Figure 8:
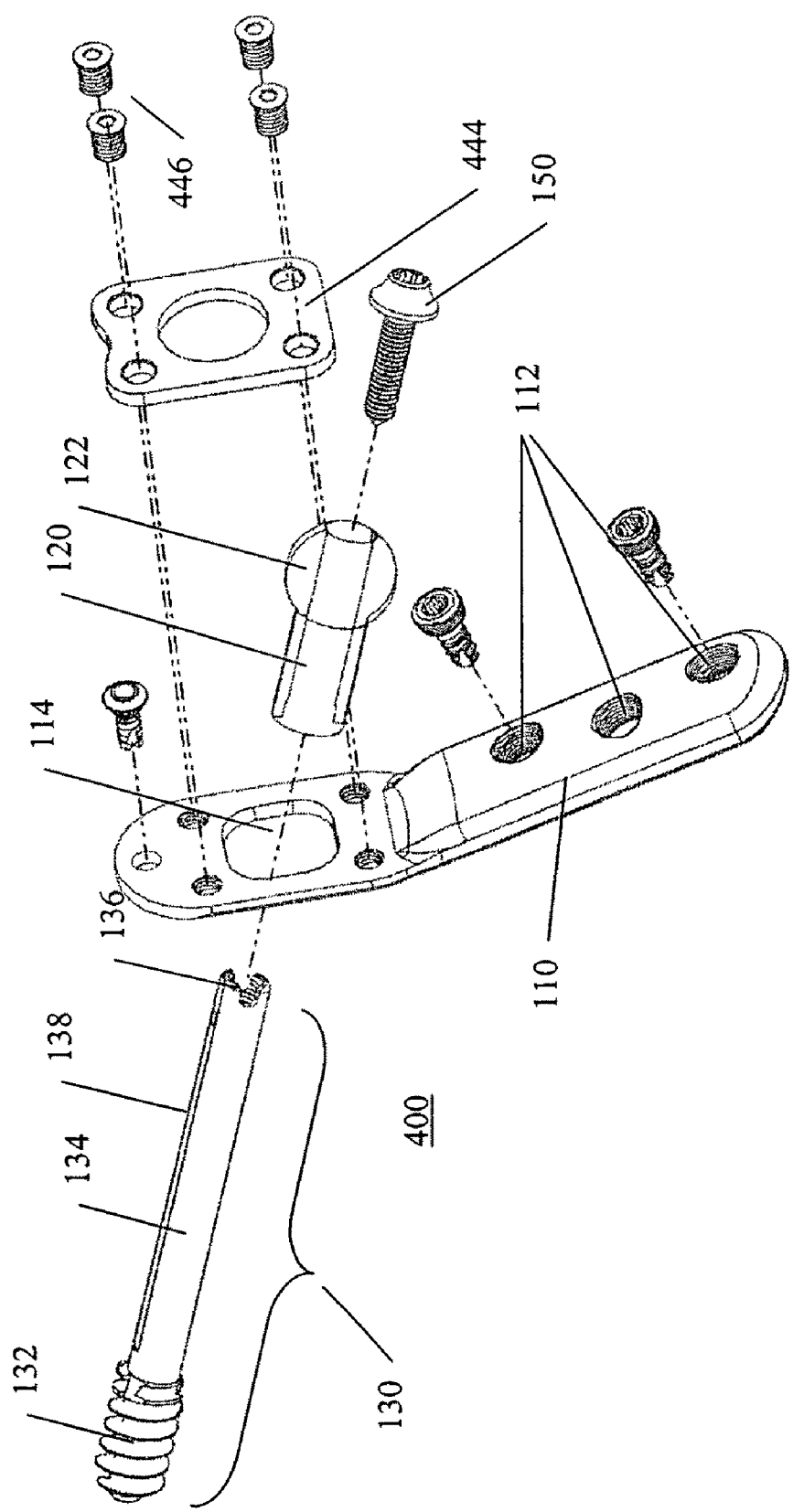
FIG. 8 depicts the polyaxial CHS assembly shown in FIG. 7, broken down into its various components, in accordance with an embodiment of the present invention.

FIG. 7 depicts aspects of a CHS assembly 400 with a polyaxial cross member in accordance with still another embodiment of the present invention. The polyaxial CHS assembly 400 functions similarly to the assemblies 100, 200, and 300 shown in FIGS. 1, 3, and 5, with like numerals indicating like elements, except for the securing mechanism 440. FIG. 8 depicts the polyaxial CHS assembly 400, broken down into its various components to further illustrate the securing mechanism 440. In this particular polyaxial CHS assembly 400, the securing mechanism 440 includes a securing element 444, such as a top plate, and one or more fastening elements 446, such as screws, that secure the barrel member 120 to an end of the side plate 110. This embodiment is different from the one shown in FIG. 2 in that the side plate 110 is not depressed around the opening 114 in order to accommodate the top plate 444. Instead, the top plate 444 is set abutted against the one end of the side plate 110 as shown in FIG. 7. Once the lag screw 130 is inserted at the proper angle, the screws 446 are tightened to press the top plate 444 against the side plate 110 and bias the ball joint 122 against the side wall of the opening 114 so that the ball joint 122 can make contact with such side wall at one or more areas to hold and retain the ball joint 122 in place at the desired orientation.

To avoid further repetition in the present disclosure, additional embodiments of a CHS assembly with a polyaxial cross member are described next without any further reference to those common components that are already described earlier.

Figure 9A:
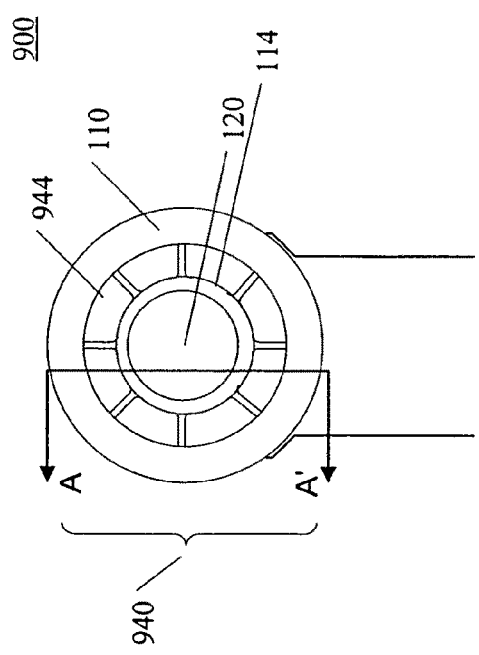
FIGS. 9A-D depict aspects of a polyaxial CHS assembly, in accordance with various embodiments of the present invention.
Figure 9B:
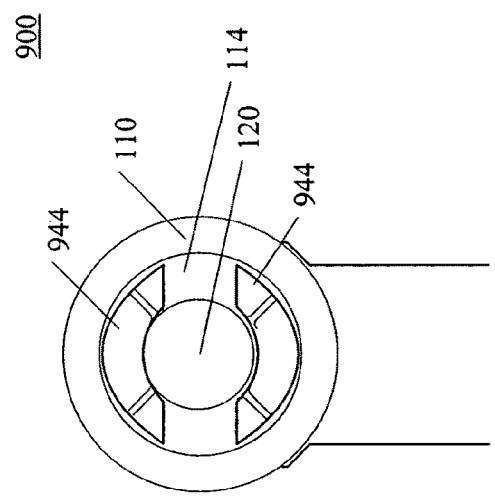

FIG. 9A depicts aspects of a polyaxial CHS assembly 900, as viewed directly into the side plate 110, having additional "press-fit sleeve" securing mechanism 940 in accordance with one embodiment of the present invention. Similar to the polyaxial CHS assembly 300 depicted in FIGS. 5-6, the side plate 110 in the polyaxial CHS assembly 900 includes an opening 114 at one end. The securing mechanism 940 includes an expandable collet 944 that can secured to the side wall of the opening 114 by another securing mechanism, such as the securing mechanism 240 shown in FIGS. 3-4 and described earlier. The expandable collet 944 can be a single-piece design, as shown in FIG. 9A, or a multiple-piece design, for example, a two-piece design as shown in FIG. 9B. The multiple-piece design of the collet 944 allows it to be used with other securing mechanisms as described later.

Figure 9C:
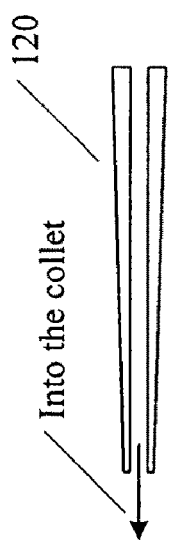

In the particular embodiments shown in FIGS. 9A-B, the barrel member 120 is tapered along its long axis. FIG. 9C depicts a cross section of the barrel member 120, as cut along its long axis towards the opening 114, showing the tapered sides. As shown in FIGS. 9A-B, as the tapered barrel member 120 is inserted, preferably with its tapered end first, into an opening in the center of the expandable collet 944 and at the desired angle to cover the lag screw 130, it causes the collet 944 to compress against the side wall of the opening 114. The pressure that the collet 944 exerts back to the tapered barrel member 120, due to contact with the larger diameter of the tapered barrel member 120 as it is further inserted into the collet 944, serves to hold and retain the barrel member 120, and thus the lag screw 130, in place at the proper angulation. Thus, the collet 944 can be used as a polyaxial joint in place of the ball joint 122 shown in FIGS. 1-8.

Figure 9D:
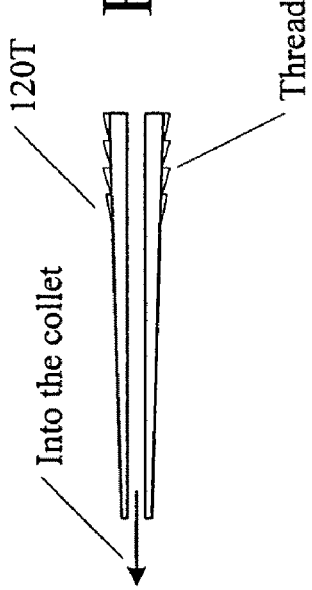

According to another embodiment for the additional "press fit sleeve" securing mechanism, the tapered barrel member 120 shown in FIG. 9C can further be threaded on its surface at one end. FIG. 9D depicts a cross section of the barrel member 120T, as cut along its long axis towards the opening 114, showing the tapered sides and threaded surface. Accordingly, the collet 944 is also threaded in the opening at its center in order to receive the threaded barrel member 120T. In this embodiment, as the barrel member 120T is inserted, preferably with its tapered end first, into the threaded center opening of the expandable collet 944, and at the desired angle to cover the lag screw 130, the threadings on the barrel member 120T eventually engages with the threadings in the expandable collet 944 and as the barrel member 120T is turned along its threadings, it causes the collet 944 to expand into the side wall of the opening 114 and secures the collet 944 to the opening 114 in the side plate 110. Also, the pressure that Collet 944 exerts back to the tapered barrel member 120, due to the threaded contact with the barrel member 120T serves to hold and retain the barrel member 120, and thus the lag screw 130, in place at the proper angle.

Figure 12:
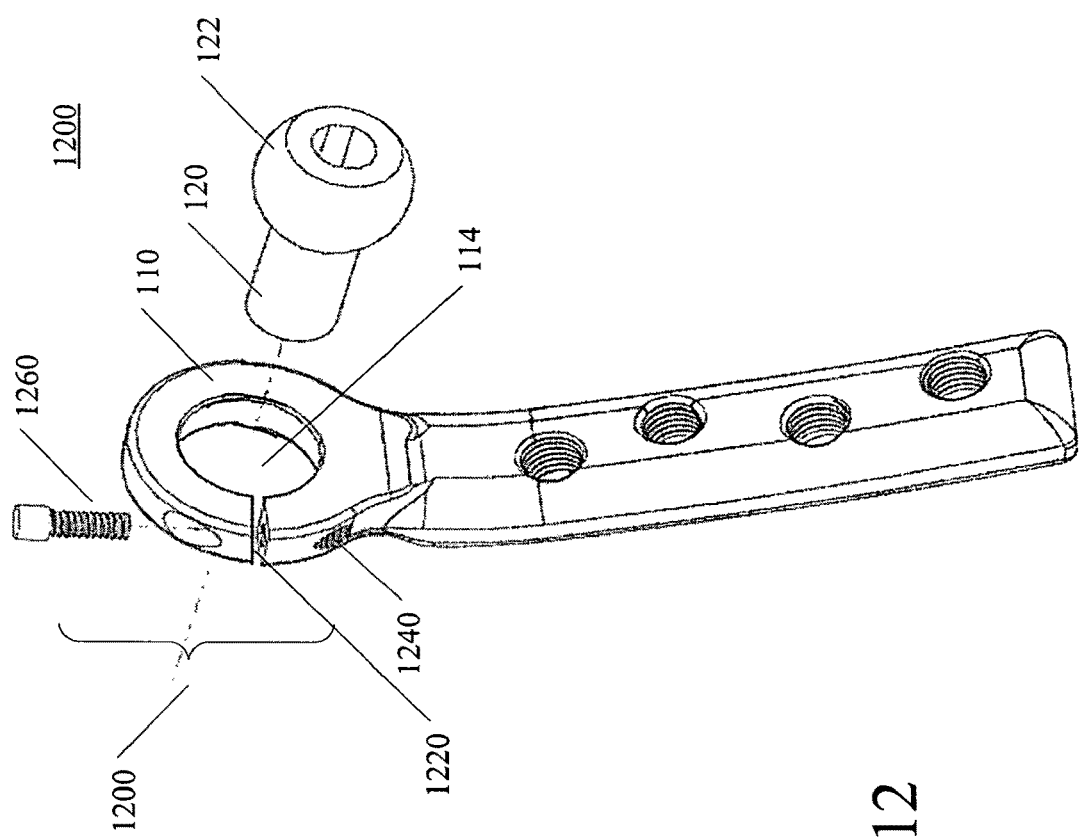
FIG. 12 depicts aspects of a polyaxial CHS assembly, in accordance with another embodiment of the present invention.

FIG. 12 depicts a polyaxial CHS assembly 1200, as viewed directly into the side plate 110, with another embodiment for a securing mechanism. Similar to some of the previously-described polyaxial CHS assemblies, the side plate 110 in the polyaxial CHS assembly 1200 includes an opening 114 at one end. It also has a gap 1220 at one portion in the side wall of the opening 110. The securing mechanism then includes a slot or hole 1240 and a fastening element 1260, such as a screw, that can be inserted into the slot 1240 to bring the separated portions of the side plate 110 together and close the gap 1220. Thus, once the lag screw 130 is at a proper angle, the barrel member 120 is inserted through the opening 114 to cover the lag screw 130 at the desired orientation, the screw 1260 is tightened or compressed in the slot 1240 to bias the ball joint 122 against the side wall of the opening 114 so that the ball joint 122 can make contact with such side wall at one or more areas to hold and retain the ball joint 122 in place at the desired orientation. Furthermore, as with the securing mechanism 240 shown in FIGS. 3-4, the securing mechanism shown in FIG. 12 can also be used to secure the expandable collet 944, shown in FIG. 9A, to the side wall of the opening 114.

Figure 13:
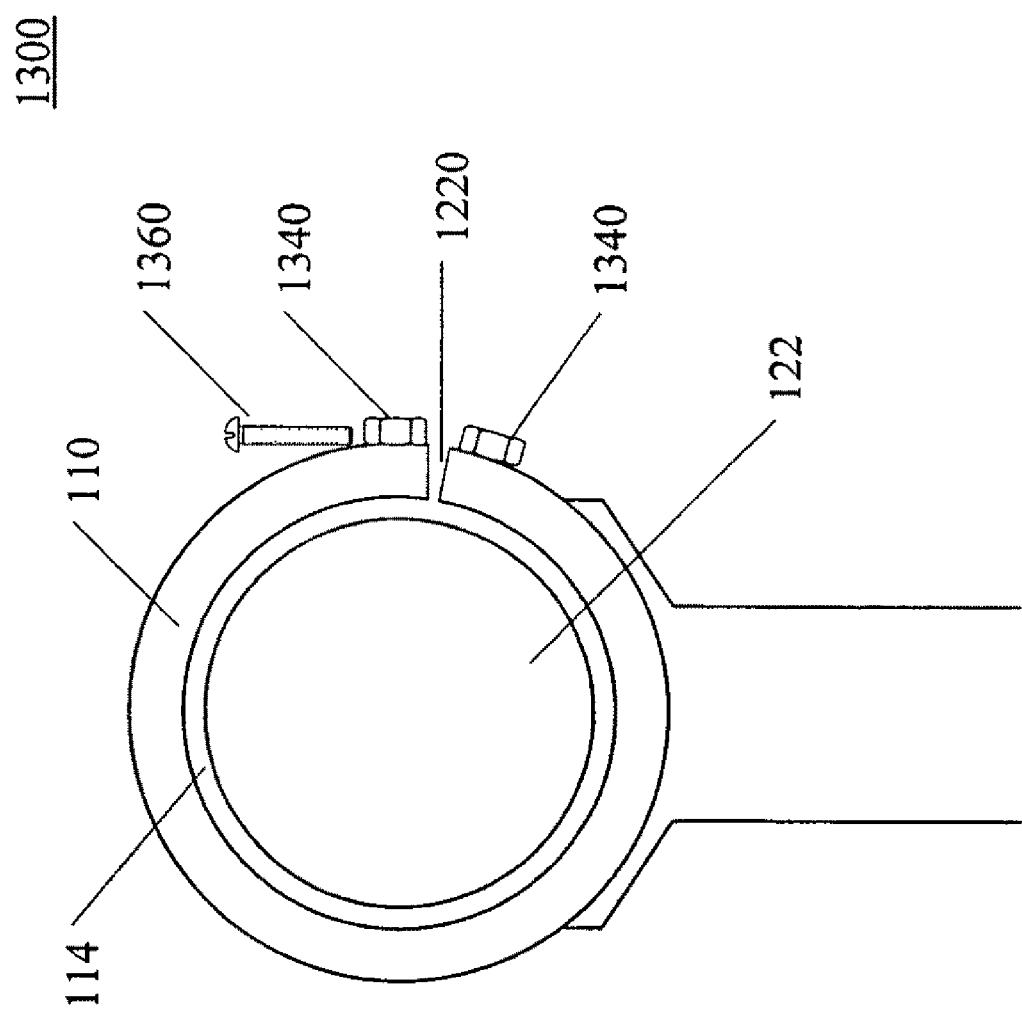
FIG. 13 depicts aspects of a polyaxial CHS assembly, in accordance with another embodiment of the present invention.

FIG. 13 depicts a polyaxial CHS assembly 1300, as viewed directly into the side plate 110, with still another embodiment for a securing mechanism. Similar to some of the previously-described polyaxial CHS assemblies, the side plate 110 in the polyaxial CHS assembly 900 includes an opening 114 at one end. As with the embodiment shown in FIG. 12, the side plate 110 also has a gap 1220 at one portion in the side wall of the opening 110. However, in place of the internal slot 1240, external slots 1340 are provided to the separated portions of the side plate 110, through which a fastening element 1360, such as a screw, can be inserted and tightened to bring the separated portions together and close the gap 1220 to hold and retain the ball joint 122 in place at the desired location, as explained earlier. In other embodiments similar to the one shown in FIG. 13, in place of the external slots 1340 and screw 1360, a cam lock, a latch, or any known locking mechanism can be arranged along the gap 1220 to bring the separated portions of the side plate 110 together and close such gap. Furthermore, as with the securing mechanism 240 shown in FIGS. 3-4, the securing mechanism shown in FIG. 13 and the above alternate embodiments can also be used to secure the expandable collet 944, shown in FIG. 9A, to the side wall of the opening 114.

Figure 14A:
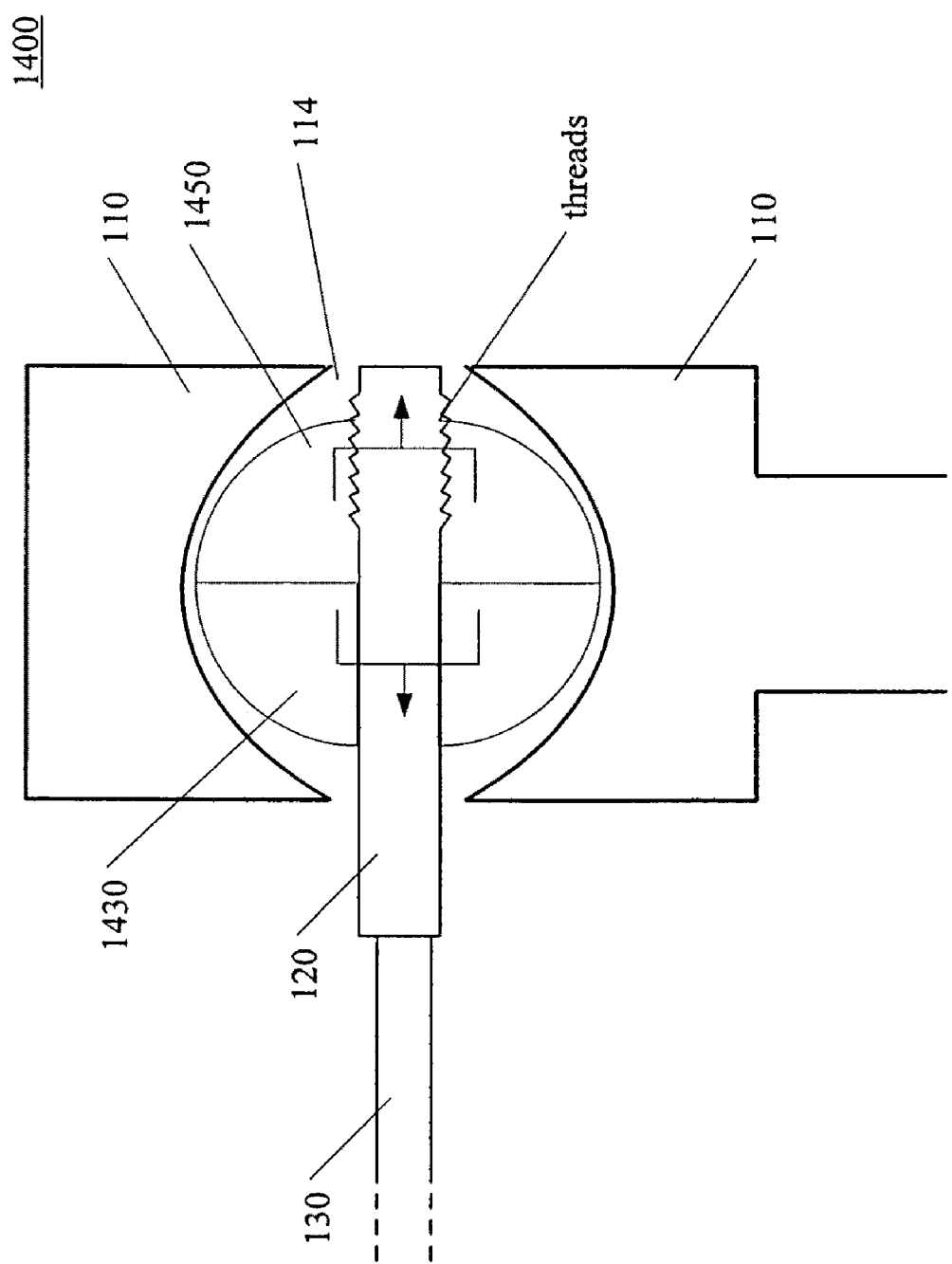
FIGS. 14A-B depict aspects of a polyaxial CHS assembly, in accordance with another embodiment of the present invention.
Figure 14B:
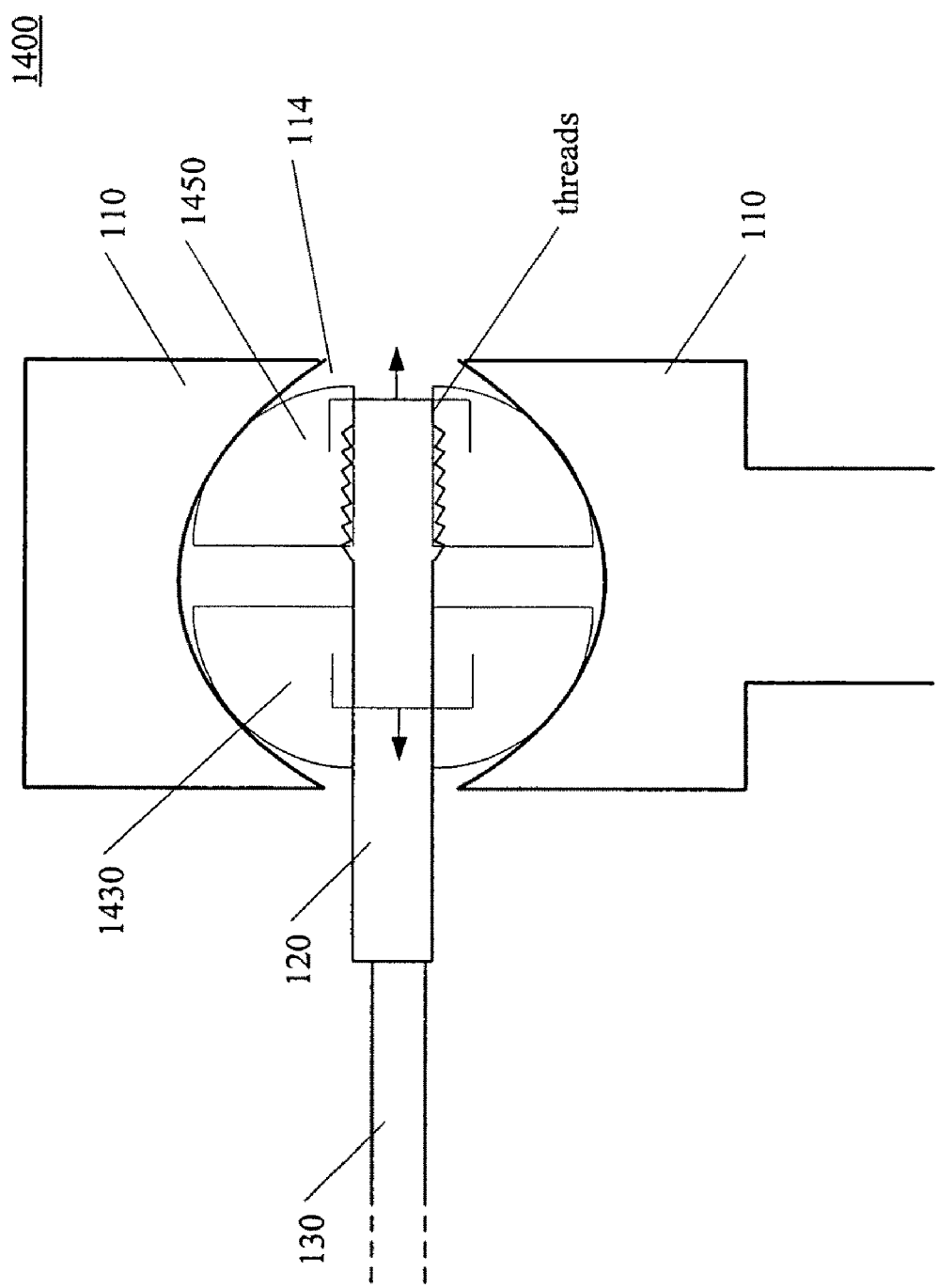

FIGS. 14A-B depict side views of a CHS assembly 1400 with a polyaxial cross member in accordance with still another embodiment of the present invention. Similar to some of the previously-described polyaxial CHS assemblies, the side plate 110 in the polyaxial CHS assembly 1400 includes an opening 114 at one end. However, FIG. 14A shows a cross-sectional view of the ball joint 122 that is constructed from two half sections 1430 and 1450. In this embodiment, the barrel member 120 can be press-fitted, welded, made integral with (i.e., as a single structure), or secured in any desired manner with either one of the half sections 1430, 1450 of the ball joint 122; e.g., the first half section 1430. The remaining half section, e.g., the half section 1450, of the ball joint 122 can be internally threaded and separate from the first half section 1430. The barrel member 120 is further threaded at one end to receive the threads of the second half section 1450 so that the first half section 1430 can be held in place as the second half section 1450 is turned to create a distance between the two half sections 1430 and 1450, as shown by the arrows in FIG. 14A. Thus, the ball joint 122, formed from two half sections, is pre-fitted into the opening 114 of the side plate 110. In operation, the lag screw 130 is first inserted at a proper angle relative to the femur to engage, for example, the femoral head. Once the proper angle is achieved, the side plate 110, with the pre-fitted barrel member 120 and ball joint 122, is introduced to the lateral side of the femur so that the barrel member 120 can be placed over the lag screw 130. Again, at this junction, the side plate 110 can be adjusted in multiple planes until it fits, preferably flush, to the side of the femur. The barrel member 120 is then turned to separate the two half sections 1430,1450 of the ball joint 122 and compress them against the edges of the opening 114, as shown in FIG. 14B, to hold and retain the ball joint 122 in place at the desired orientation. The surgery is continued and completed in a standard manner.

FIG. 15 depicts another embodiment for a CHS assembly 1500 with a polyaxial cross member. In this embodiment, in place of a ball joint 122 is a polyaxial joint that is formed from two half sections 1530 and 1550. The side plate 110 is contoured at the opening 114 (hidden from view) to accommodate the contours of the two half sections 1530 and 1550. For example, in the particular CHS assembly 1500, the side plate 110 at the opening 114 and the two half sections 1530 and 1550 are curved. The barrel member 120 can be press-fitted, welded, made integral with (i.e., as a single structure), or secured in any desired manner with the first half section 1530. The second half section 1550 can be internally threaded and separated from the first half section 1550 by the side plate 110. The barrel member 120 is further threaded at one end to allow the threaded second half section 1550 to engage the barrel member 120. Once the lag screw 130 is set at a proper angle, the barrel member 120 with the attached half section 1530 can be placed over the lag screw 130. Next, the side plate 110 is attached to the femur so that the barrel member 120 protrudes through the opening 114 in the side plate 110. In this embodiment, the opening 114 is larger than the barrel member 120 to enable the latter to be set at a desired orientation. Thus, while the first half section 1530 is held in place by the barrel member 120, the second half section 1550 is threaded onto the barrel member 120 to compress the side plate 110 in between the two half sections 1530 and 1550 of the polyaxial joint. The resulting compression locks the barrel member 120 in place at the desired orientation. In an alternative embodiment, the barrel member 120 can be press-fitted, welded, made integral with (i.e., as a single structure), or secured in any desired manner with the second half section 1550, and the first half section 1530 is internally threaded. The barrel member 120 is also threaded on its surface to engage the threaded first half section 1530 so that when the barrel member 120 is turned, the second half section 1550 is compressed against the side plate 110, and the first half section 1530 is drawn also compress against side plate (110) and hold the barrel member 120 in place at the desired orientation.

Alternative embodiments are further contemplated wherein the polyaxial joint is neither a ball joint or those shown in FIG. 15, but a cylinder that can achieve uni-axial motion based on its long axis, and the lag screw 130 can be set at any angle along that singular axis of motion.

Figure 17B:
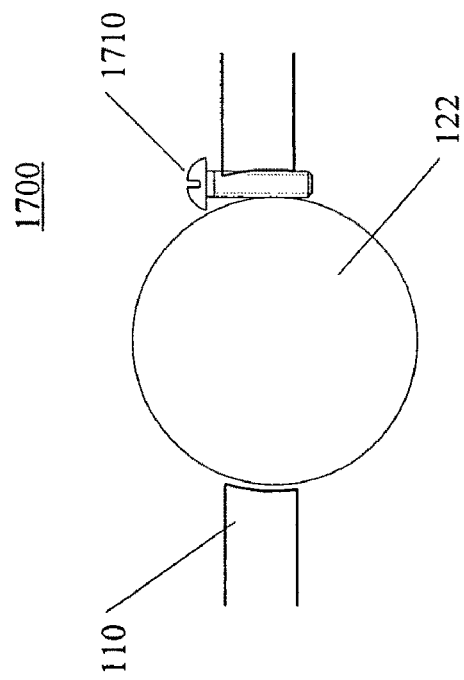
FIGS. 17A-B depict aspects of a polyaxial CHS assembly, in accordance with another embodiment of the present invention.
Figure 17A:
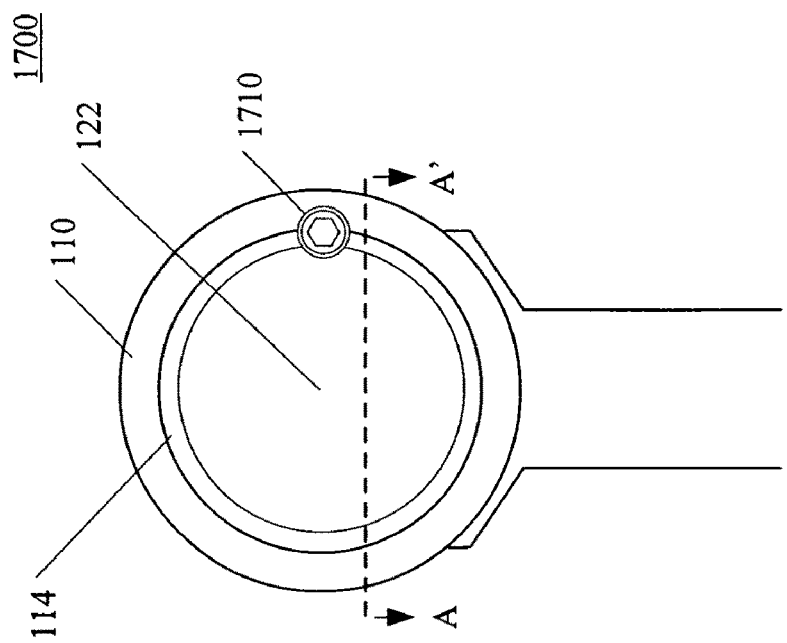

FIGS. 17A-B depict aspects of a polyaxial CHS assembly 1700, as viewed directly into the side plate 110, with another embodiment for a securing mechanism. In this embodiment, the securing mechanism includes an interference element 1710, such as a screw, that can be inserted in the opening 114 between the ball joint 122 and the side plate 110 anywhere along the side wall of the opening 114 such that it interferes with the movement of the ball joint 122. FIG. 17B depicts a cross section taken along the line A-A' of FIG. 17A with the screw 1710. The pressure resulting from the interference caused by the screw 1710 prevents the ball joint 122 from moving. Alternatively, the ball joint 122 and/or the screw 1710 can deform as the latter is tightened or compressed in the opening 114 so that such deformation prevents the ball joint 122 from moving and holds and retains the ball joint 122 in place at the desired orientation. Although only one interference element 1710 is shown in FIGS. 17A-B, alternative embodiments are contemplated wherein there are more than one interference elements 1710 that can be inserted along the side wall of the opening 114 to provide additional holds on the ball joint 122 and withstand the high weight-bearing loads on the lag screw 130 as discussed earlier. Furthermore, the securing mechanism shown in FIGS. 17A-B and the above alternate embodiments can also be used to secure the multi-section expandable collet 944, shown in FIG. 9B, to the side wall of the opening 114.

Figure 18B:
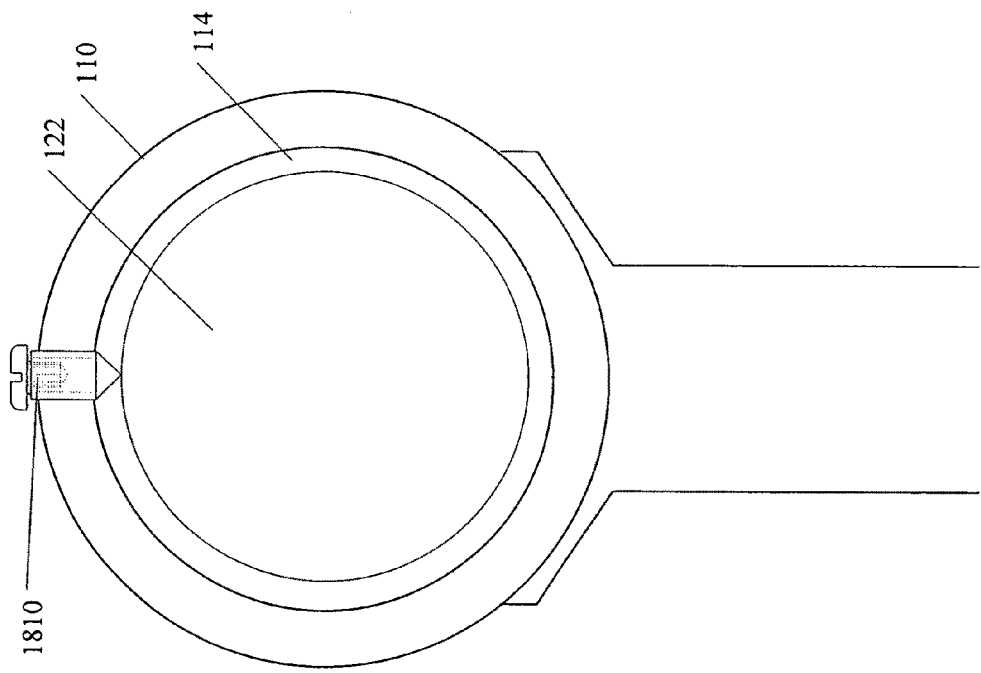
FIGS. 18A-B depict aspects of a polyaxial CHS assembly, in accordance with another embodiment of the present invention.
Figure 18A:
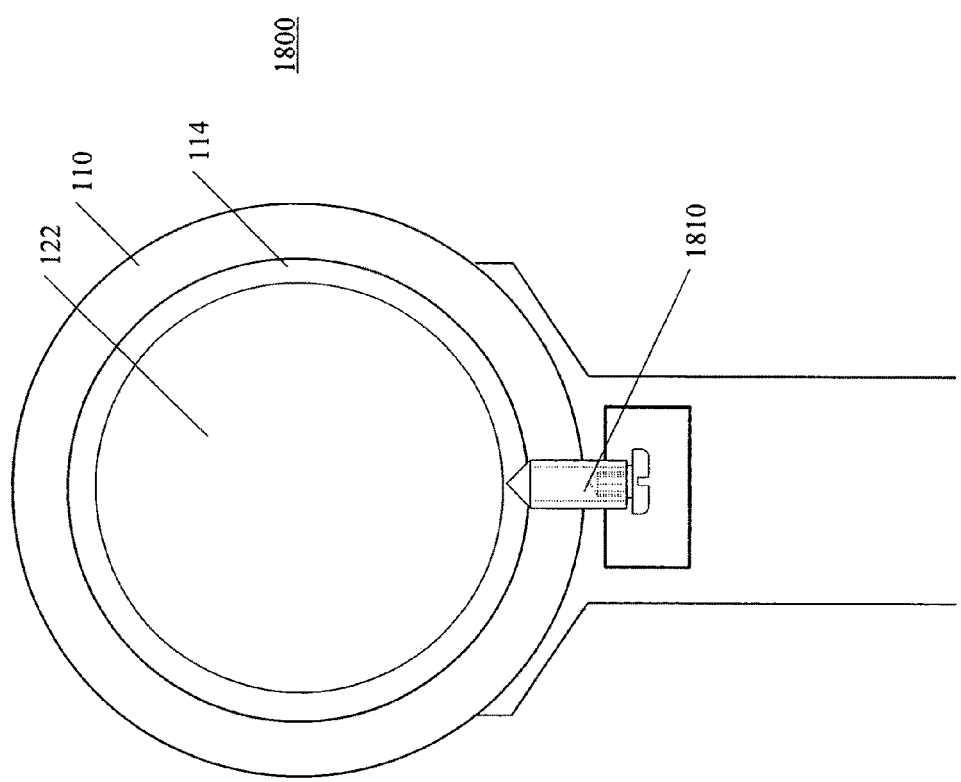

FIGS. 18A-B depict aspects of a polyaxial CHS assembly 1800, as viewed directly into the side plate 110, with another embodiment for a securing mechanism, which employs an interference concept similar to the above embodiment in FIGS. 17A-B to lock the ball joint 122 in place. In this embodiment, the securing mechanism also includes an interference element 1810, such as a screw, that originates from the side plate 110 and engages the ball joint 122 in the opening 114 of the side plate 110. The screw 1810 can be situated anywhere along the perimeter of the opening 114 in order to engage the ball joint 122. It can protrude through the side wall of the opening 114 or from an area next to such side wall. As shown in the FIGS. 18A-B, the screw 1810 is applied against the ball joint 122, and the resulting pressure prevents the later from moving. Alternatively, due to the forced contact between the screw 1810 and the ball joint 122, the contacting areas of both elements can be deformed and prevent the ball joint 122 from moving. As further shown in FIGS. 18A-B, the screw 1810 can be located anywhere along the side wall 114 so long as it can make contact with the ball joint 122. Although only one interference element 1810 is shown in FIGS. 18A-B, alternative embodiments are contemplated wherein there are more than one interference elements 1810 that can be inserted along the side wall of the opening 114 to provide additional holds on the ball joint 122 and withstand the high weight-bearing loads on the lag screw 130 as discussed earlier. Furthermore, the securing mechanism shown in FIGS. 18A-B and the above alternate embodiments can also be used to secure the multi-section expandable collet 944, shown in FIG. 9B, to the side wall of the opening 114.

Figure 19:
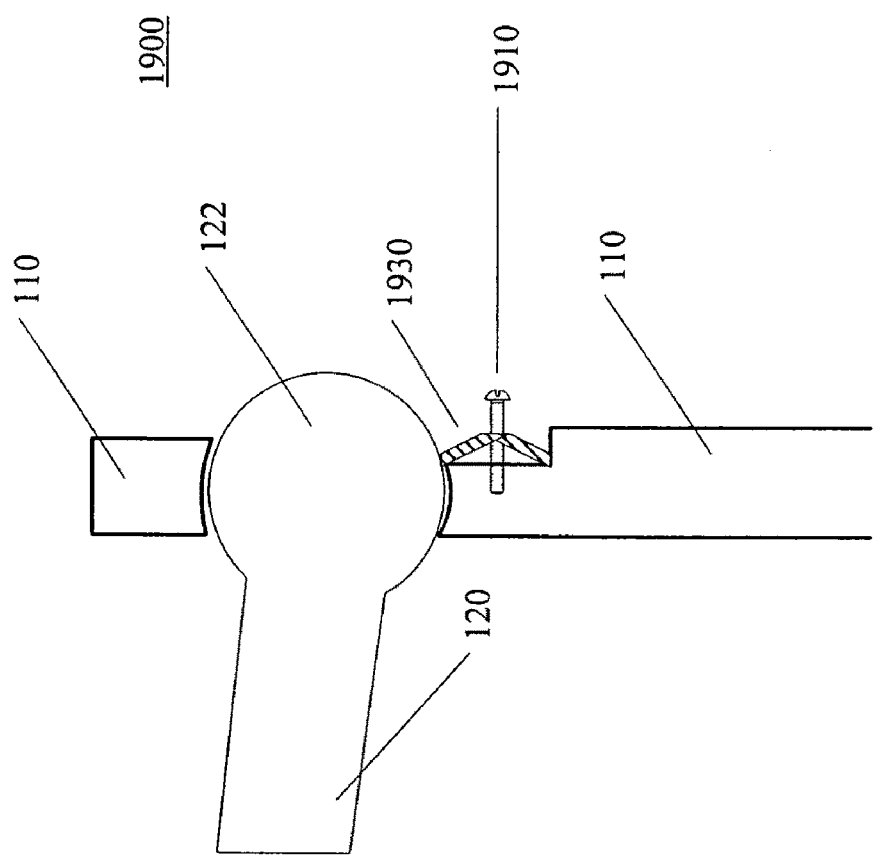
FIG. 19 depicts aspects of a polyaxial CHS assembly, in accordance with another embodiment of the present invention.

FIG. 19 depicts aspects of a polyaxial CHS assembly 1900, as viewed directly into the side plate 110, with another embodiment for a securing mechanism. In this embodiment, the securing mechanism is situated in a similar position to that of the screw 1810 shown in FIGS. 18A, B, i.e., anywhere along the side wall of the opening 114. It includes a fastening element 1910, such as a screw, and a spring-loaded member 1930. The screw 1910 is inserted through an opening in the spring-loaded member 1930 to exert pressure and straighten out the later. As the spring-loaded member 1930 is straightened, it compresses the ball joint 122 between the side wall of the opening 114 in the side plate 110 and the spring-loaded member and holds and retains the ball joint in place at the desired orientation for the barrel member 120. Furthermore, the securing mechanism shown in FIG. 19 can also be used to secure the multi-section expandable collet 944, shown in FIG. 9B, to the side wall of the opening 114.

Figure 20:
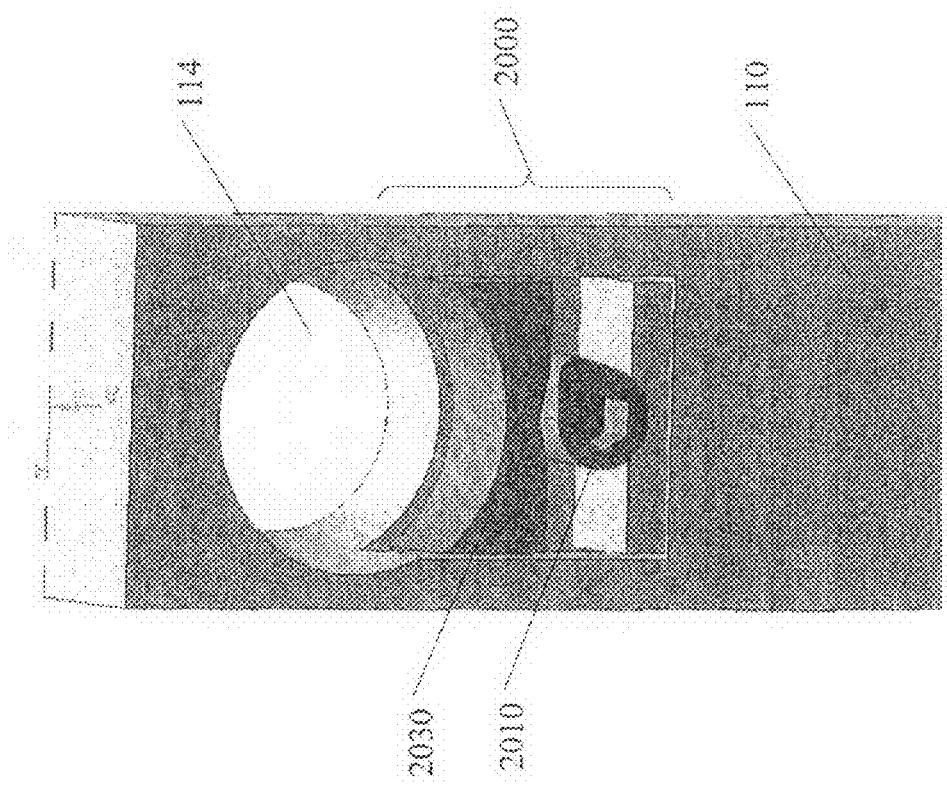
FIG. 20 depicts aspects of a polyaxial CHS assembly, in accordance with another embodiment of the present invention.

FIG. 20 depicts aspects of a polyaxial CHS assembly 2000, as viewed directly into the side plate 110, with another embodiment for a securing mechanism. In this embodiment, the securing mechanism 2000 is a cam lock having a rotating member 2010 and a pressure member 2030. The rotating member 2010 can be rotated to apply force to the pressure member 2030, which then engages and compresses the ball joint 122 between the pressure member 2030 and a side wall of the opening 114 to hold and retain the ball joint 122 in place at the desired orientation. The rotating member 2010 can include an overcenter feature so that it retains itself in place against the pressure member 2030 once rotated beyond a certain position.

In the various embodiments of a polyaxial CHS assembly described above, the inner surface or side wall of the opening 114 can have various geometrical configurations. For example, FIG. 10A depicts a cross section of the opening 114 as taken from line A-A' in FIG. 9, wherein the opening 114 is enclosed by a curved or spherical side wall 1015. The side wall 1015 can have the same curvature as the ball joint 122 so that when the latter is inserted into the opening 114 and set at a desired orientation, the ball joint 122 can contact the side wall 1015 at one or more areas to assist one of the aforementioned securing mechanisms in retaining the ball joint 122 in place at the desired orientation. In another example, as also shown in FIG. 10A, the opening 114 is enclosed by a tapered side wall 1025, which have protrusions 1027 at the edges of the side wall to help grip, compress, or make contact with the ball joint 122 at least two points to assist one of the aforementioned securing mechanisms in retaining the ball joint 122 in place at the desired location. The protrusions 1027 can be configured, positioned, and oriented as desired. In still another example, the side wall of the opening 114 in the side plate 110 shown in FIGS. 2, 4, 6, 8, 12, 13, 16, 19, and 20 can be tapered in, as the side wall runs from the side plate's front surface (facing out of the femur and shown in the figures) to its back surface (facing into the femur and hidden in the figures) to provide a secure seating for the ball joint 122. Furthermore, the top plates 144, 344, and 444 shown in FIGS. 2, 6, and 8 can have their openings tapered in the opposite direction, i.e., the side wall of such an opening is tapered in as the side wall runs from the top plate's back surface (facing into the femur and hidden in the figures) to the top plate's front surface. In combination, the tapered opening 114 and the tapered opening of the top plate in FIG. 2, 6, or 8 provide additional hold on the ball joint 122 therebetween.

According to an embodiment of the present invention, the side wall of the opening 114, which can have various geometrical configurations, can further include one or more protrusions 1030, e.g., raised bumps, as shown in FIG. 10B, and the ball joint 122 correspondingly includes one or more indentations 1040, e.g., dimples, on its surface (e.g., similar to a golf ball). FIG. 10B shows only some of the protrusions 1030 and indentations 1040 for illustration purposes. It should be noted that the protrusions 1030 can be distributed uniformly throughout the side wall of the opening 114; likewise, the indentations 1040 can be distributed uniformly throughout the surface of the ball joint 122. Alternatively, the protrusions 1030 can be distributed uniformly throughout the surface of the ball joint 122, and the indentations 1040 can be distributed uniformly through the side wall of the opening 114. The cooperation of the protrusions 1030 and indentation 1040, wherever they may be distributed, can limit the ball joint 122 to preset angulations. However, such cooperation can provide an additional hold on the ball joint 122 at the preset angulations and assist the lag screw 130 in withstanding the high weight-bearing loads mentioned earlier. Thus, the densities of the protrusions 1030 and the indentations 1040 and their locations on the side wall of the opening 114 and the surface of the ball joint 122 can be strategically chosen to provide desired angulations of the ball joint 122 about desired axes, wherein such angulations and desired axes are found useful in accommodating the human anatomy for fracture treatments, such as sliding compression. The ball joint 122 is then rotated to a desired location for the barrel 120, and one or more of the protrusions 1030 are aligned and latched with the one or more indentations 1040 on the surface of the ball joint 122 to further hold the ball joint 122 at the desired orientation.

In some or all of the various embodiments of a polyaxial CHS assembly described above, wherein the ball joint 122 is employed, the ball joint 122 further can be a collet-type ball joint with one or more slots or slits for expansion. FIG. 11 depicts a cross section of the ball joint 122 having expansions slots 1221 that are preferably arranged in a general direction along the axis of insertion of the ball joint 122 into the opening 114. As the ball joint 122 is biased against the opening 114 to hold it in place at a desired orientation, the ball joint 122 compresses against the expansions slots 1221, which will counter with an expansion force (due to their spring-like actions) to further press the ball joint 122 against the opening 114 and assist with the holding of the ball joint 122 at the desired orientation.

Although some or all of the above-described embodiments of a polyaxial CHS assembly depict a rectangular, square, or circular opening 114 in the side plate 110 to accommodate the ball joint 122, other embodiments are contemplated wherein the opening 114 can be circular, elliptical, polygonal, or any other shape, or any combination thereof so as to create a proper seat for the ball joint 122.

Furthermore, although some or all of the above-described embodiments of a polyaxial assembly depict the ball joint 122 as a part of or integral to the barrel member 120, alternative embodiments are contemplated wherein the ball joint 122 is a separate component from the barrel member 120 but attached, affixed, or secured to one end of the barrel member 120 in any desired manner.

Still furthermore, although some or all of the aforementioned embodiments of a polyaxial CHS assembly have been described wherein screws are used as fastening elements, alternative embodiments are contemplated wherein each of the mentioned fastening element can be a straight screw, a tapered screw, a tapered pin, a nail, a rivet, a bolt (and nut), or any element that can be used for fastening purposes and/or contacting the ball joint 122 to exert pressure or compression and/or hinder movement of the ball joint 122.

Figure 21:
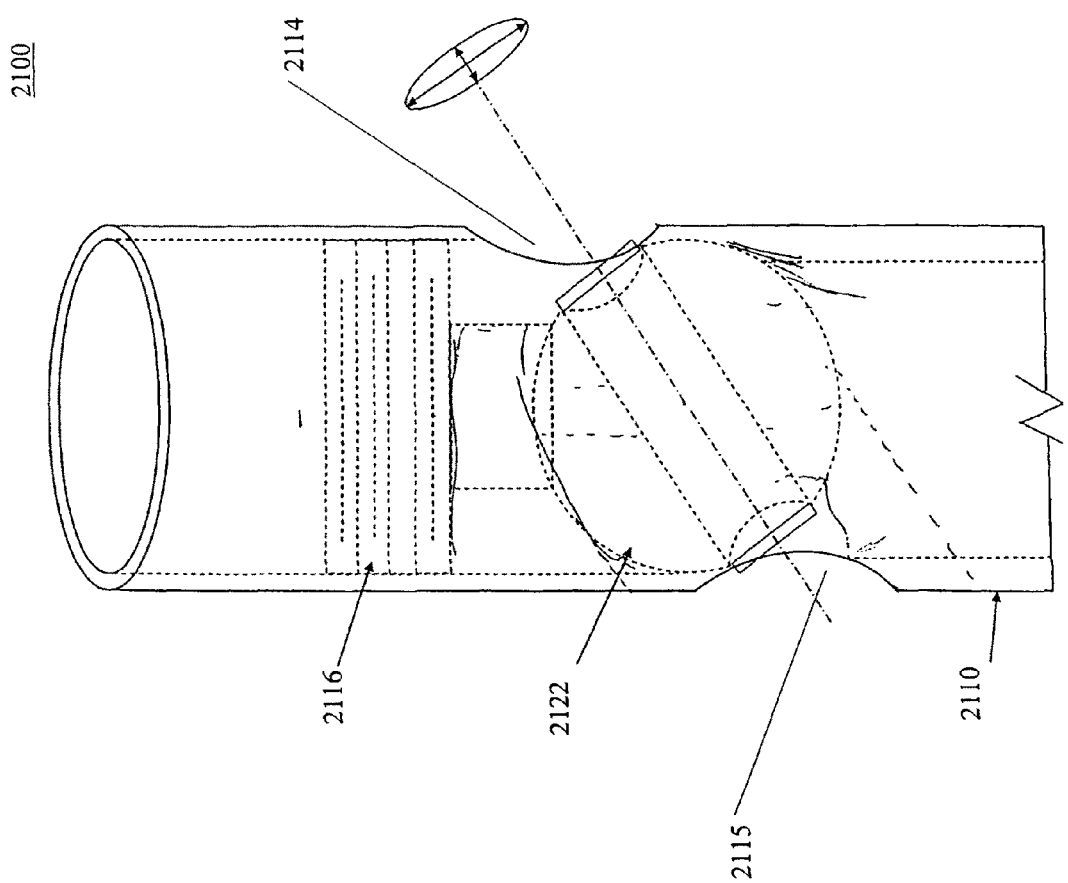
FIG. 21 depicts aspects of a polyaxial intramedullary (IM) nail assembly, in accordance with another embodiment of the present invention.

FIG. 21 depicts another femoral fracture device, namely, an intramedullary nail (IM) assembly 2100, with a polyaxial cross member in accordance with an embodiment of the present invention. The IM nail assembly 2100 includes an IM rod 2110 that has a proximal end and a stem distal thereto (not shown). Closer to the proximal end are the openings 2114 and 2115 opposite to one another. The IM nail assembly 2100 further includes a ball joint 2122, a securing mechanism 2116, a cross member (not shown) which can maintain sliding contact with the ball joint 2212 to allow sliding compression of the fracture being treated, and a compression member (not shown) on the opposite side of the IM rod 2110 that extends through the opening 2115 and the ball joint 2122 to engage the cross member.

The securing mechanism 2116, such as a set screw, is configured to secure the ball joint 2122 in place. It can be a straight screw, a tapered screw, a straight pin, a tapered pin, a nail, or any element that can exert pressure on the ball joint 2122 and hinder movement of such ball joint. The cross member in the IM nail assembly 2100 also extends through the femoral neck, across the fracture line, and into the femoral head; thus, it functions similarly to the cross member 130 shown in the various polyaxial compression hip screw assemblies described earlier. The compression member can be adjusted in order to adjust the compression (reduction) of the fracture and thus functions similarly to the compression member 150 shown in the various polyaxial compression hip screw assemblies described earlier.

According to one embodiment of the present invention, the IM nail assembly 2100 is structurally similar in some ways to a conventional IMHS assembly as described in, for example, U.S. Pat. No. 5,032,125 issued on Jul. 16, 1991, to Durham et al., which is herein incorporated by reference in its entirety, except that the conventional barrel in the IMHS assembly that is used to receive the cross member is now replaced with the ball joint 2122 with a through bore. Alternatively, the IM nail assembly 2100 can further include a barrel extension that is structurally and functionally similar to a barrel member 120 in one of the aforementioned polyaxial CHS assembly, whereby such barrel extension protrudes out of IM rod 2110 through the opening 2114. Also, the internal design of the IM rod 2110 is configured to receive the ball joint 2122, which articulates within the IM rod 2110 and is locked in place with the setting member 2116. The through bore in the ball joint 2122 is configured to receive the cross member via the opening 2114 in the IM rod 2110. In operation, the IM rod 2110 is first inserted into the marrow canal of the femur. Next, the cross member is inserted through the femur, the opening 2115, and the ball joint 2122 in the IM rod 2110, and out through the opening 2114 to the femoral head at a proper angle. Once the proper angle is achieved, the setting member 2116 exerts pressure (e.g., is tightened or compressed) on the ball joint 2122 to lock the ball joint 2122, and consequently the cross member, in place at the desired orientation.

Accordingly, the polyaxial IM nail assembly 2100 functions similarly to the above-described polyaxial compression hip screw assemblies in that it allows angulation and anteversion/retroversion of the cross member.

Figure 22:
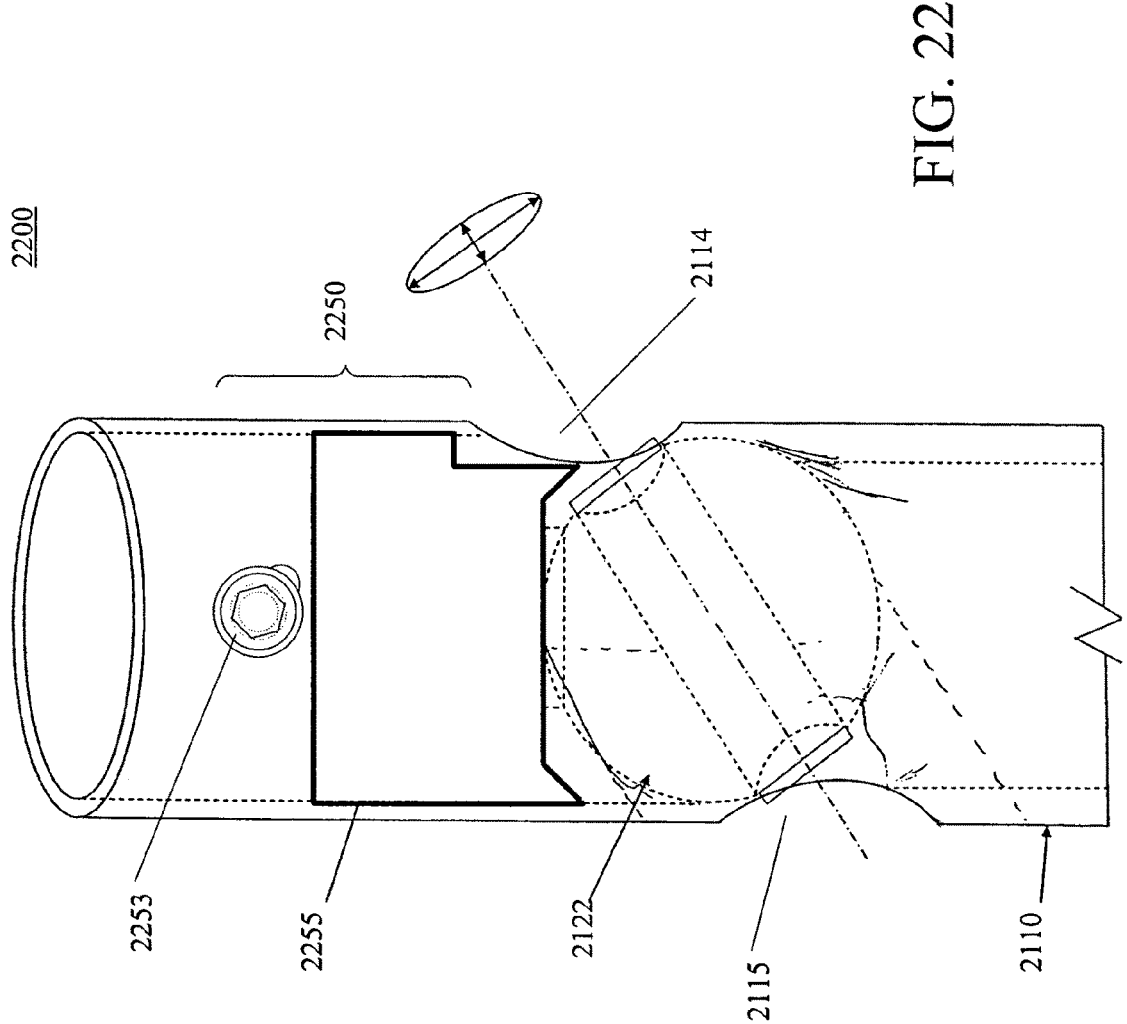
FIG. 22 depicts aspects of a polyaxial intramedullary (IM) nail assembly, in accordance with another embodiment of the present invention.

FIG. 22 depicts a polyaxial IM nail assembly 2200 in accordance with another embodiment of the represent invention. The IM nail assembly 2200 is structurally and functionally similar to the IM nail assembly 2100 depicted in FIG. 2, except that a cam lock 2250 is used in place of the setting member 2116 to lock the ball joint 2122 at the desired orientation. The cam lock 2250 is similar to one depicted in FIG. 20 in that it also includes a rotating member 2253 and a pressure member 2255. Again, the rotating member 2053 can be rotated to push up the pressure member 2255, which then engages and compresses the ball joint 122 to prevent movement on the desired orientation. The rotating member 2253 can include an overcenter feature so that it retains itself in place against the pressure member 2030 once rotated beyond a certain position.

As with the side wall in the opening 114 of the above-described embodiments for a polyaxial CHS assembly, the seating (e.g., inner wall of the IM rod 2110) for the ball joint 2122 inside the IM rod 2110 for the above-described various embodiments of an IM nail assembly can have various geometrical configurations, such as spherical or tapered. For instance, the seating can be a conical tapered section that can wedge the ball joint 2122 in place to lock it as the setting member 2116 or cam lock 2250 exerts pressure on the ball joint 2122. To enhance the locking of the ball joint 2122, such seating can further include one or more protrusions, e.g., raised bumps, and the ball joint 122 correspondingly includes one or more indentations 1040, e.g., dimples, on its surface (e.g., similar to a golf ball), as described earlier with reference to FIG. 10B. Additionally, the ball joint 2122 can be a collet-type ball with one or more expansion slots as previously shown in FIG. 9D to further enhance the locking of the such ball joint.

According to additional embodiments of the present invention, the above polyaxial designs for the cross member in an IM nail assembly can be applied to other fastening and/or anchoring elements in the nail assembly as well. For example, ball joints similar to ball joints 2122 (in above embodiments for a polyaxial IM nail assembly) or ball joints 122 (in above embodiments for a polyaxial CHS assembly) can be used with anchoring elements to optimize their orientation in securing the distal end of the IM rod 2116 within the marrow canal of the femur. U.S. Pat. No. 4,827,917 issued on May 9, 1989 to David L. Brumfield, which is herein incorporated by reference in its entirety, discloses such anchoring elements with which ball joints can be used. Furthermore, the IM nail assembly as disclosed in the same patent includes two cross members; one is a lag screw and the other is an additional anchoring element; thus, alternative embodiments are contemplated wherein the ball joint 2122 can include more than one through bore (and thus more than one pair of openings 2114, 2115) to accommodate multiple cross members, or the IM rod 2116 can be configured to accommodate more than one ball joint for the multiple cross members. Furthermore, the ball joint 2122 can include more than one through bore, one to accommodate a cross member and another one to accommodate the guide wire for the cross member.

Although the invention has been described with reference to these preferred embodiments, other embodiments could be made by those in the art to achieve the same or similar results. Variations and modifications of the present invention will be apparent to one skilled in the art based on this disclosure, and the present invention encompasses all such modifications and equivalents.

The invention claimed is:

1. An intramedullary nail assembly, comprising:
an intramedullary rod having a proximal end, a distal end, a wall defining an elongated hollow enclosure, a first through opening in the wall spaced from the proximal and distal ends and closer to the proximal end than the distal end, and a second opposing through opening in the wall spaced from the proximal and distal ends and further from the proximal end than the first through opening;
a spherical ball joint in the hollow enclosure of the intramedullary rod having a through bore that opens to the first and second through openings in the wall; and
a securing mechanism in the hollow enclosure that engages the spherical ball joint and is configured to lock the ball joint at a predetermined orientation relative to the first and second through openings in the wall, the securing mechanism having a cam lock including a rotating member and a pressure member, the rotating member being rotatable to push the pressure member into engagement with the spherical ball joint to lock the ball joint at the predetermined orientation.

2. The intramedullary nail assembly of claim 1, wherein the second through opening in the wall is closer to the proximal end than to the distal end.

3. The intramedullary nail assembly of claim 1, wherein the wall is cylindrical.

4. The intramedullary nail assembly of claim 1, wherein the securing mechanism comprises a set screw that engages the spherical ball joint to lock the ball joint at the predetermined orientation.

5. The intramedullary nail assembly of claim 1, further comprising a cross member inserted through the first and second through openings in the wall and the through bore in the spherical ball joint.

6. The intramedullary nail assembly of claim 1, wherein the wall is tapered in the vicinity of the spherical ball joint.

7. An intramedullary nail assembly, comprising:
an intramedullary rod having a proximal end, a distal end, a wall defining an elongated hollow enclosure, a first through opening in the wall spaced from the proximal and distal ends and closer to the proximal end than the distal end, and a second opposing through opening in the wall spaced from the proximal and distal ends and further from the proximal end than the first through opening;
a spherical ball joint in the hollow enclosure of the intramedullary rod having a through bore that opens to the first and second through openings in the wall;
a securing mechanism in the hollow enclosure that engages the spherical ball joint and is configured to lock the ball joint at a predetermined orientation relative to the first and second through openings in the wall; and
wherein the hollow enclosure has a first diameter at locations closer to the proximal end than the first and second openings are to the proximal end, and a second diameter at locations closer to the distal end than the first and second openings are to the distal end, the first diameter being larger than the second diameter.

8. The intramedullary nail assembly of claim 7, wherein the spherical ball joint has a diameter that is larger than the second diameter.

9. An intramedullary nail assembly, comprising:
an intramedullary rod having a proximal end, a distal end, a wall defining an elongated hollow enclosure, a first through opening in the wall spaced from the proximal and distal ends and closer to the proximal end than the distal end, and a second opposing through opening in the wall spaced from the proximal and distal ends and further from the proximal end than the first through opening;
a spherical ball joint in the hollow enclosure of the intramedullary rod having a through bore that opens to the first and second through openings in the wall;
a spherical or tapered seating for the ball joint defined by the hollow enclosure; and
a securing mechanism in the hollow enclosure that engages the spherical ball joint and is configured to lock the ball joint at a predetermined orientation relative to the first and second through openings in the wall, the securing mechanism having a cam lock including a rotating member and a pressure member, the rotating member being rotatable to push the pressure member into engagement with the spherical ball joint to lock the ball joint at the predetermined orientation.

10. The intramedullary nail assembly of claim 9, wherein the seating comprises a conical tapered section in the hollow enclosure.

11. The intramedullary nail assembly of claim 10, wherein the spherical ball joint comprises surface indentations or slots.

12. The intramedullary nail assembly of claim 9, wherein the securing mechanism comprises a set screw that engages the spherical ball joint to lock the ball joint at the predetermined orientation.

13. The intramedullary nail assembly of claim 9, further comprising a cross member inserted through the first and second through openings in the wall and the through bore in the spherical ball joint.

* * * * *